US006387404B2

(12) United States Patent
Oshlack et al.

(10) Patent No.: US 6,387,404 B2
(45) Date of Patent: May 14, 2002

(54) IMMEDIATE RELEASE TABLET CORES OF INSOLUBLE DRUGS HAVING SUSTAINED-RELEASE COATING

(75) Inventors: Benjamin Oshlack, New York, NY (US); Mark Chasin, Manalapan, NJ (US)

(73) Assignee: Euro-Celtique S.A., Luxembourg (LU)

( * ) Notice: Subject to any disclaimer, the term of this patent is extended or adjusted under 35 U.S.C. 154(b) by 0 days.

(21) Appl. No.: 09/777,466

(22) Filed: Feb. 6, 2001

Related U.S. Application Data

(60) Continuation of application No. 09/505,935, filed on Feb. 14, 2000, now Pat. No. 6,210,714, which is a continuation of application No. 08/467,575, filed on Jun. 6, 1995, now Pat. No. 6,024,982, which is a division of application No. 08/156,460, filed on Nov. 23, 1993, now Pat. No. 5,500,227.

(51) Int. Cl.[7] .............................. A61K 9/38; A61K 9/32; A61K 9/36; A61K 9/34; A61K 9/42
(52) U.S. Cl. ..................... 424/480; 424/474; 424/482; 424/476; 424/477; 424/481
(58) Field of Search ................................ 424/468, 474, 424/475, 479, 480, 482, 476, 477, 481

(56) References Cited

U.S. PATENT DOCUMENTS

| 2,714,084 A | 7/1955 | Oertel et al. ................... 167/82 |
| 3,184,386 A | 5/1965 | Stephenson ................... 167/82 |
| 3,600,495 A | 8/1971 | Oertel et al. ................... 424/31 |
| 4,557,925 A | * 12/1985 | Lindahl et al. ................ 424/19 |
| 4,716,041 A | 12/1987 | Kjornaes et al. ............. 424/468 |
| 4,752,470 A | 6/1988 | Mehta ........................ 424/458 |
| 4,777,050 A | 10/1988 | Vadino ....................... 424/468 |
| 4,840,799 A | 6/1989 | Appelgren et al. .......... 424/493 |
| 4,892,741 A | 1/1990 | Ohm et al. ................... 424/479 |
| 5,122,384 A | 6/1992 | Paradissis et al. ........... 424/451 |
| 5,133,974 A | 7/1992 | Paradissis et al. ........... 424/480 |
| 5,286,493 A | 2/1994 | Oshlack et al. .............. 424/468 |
| 5,580,578 A | 12/1996 | Oshlack et al. .............. 424/468 |
| 6,024,982 A | 2/2000 | Oshlack et al. .............. 424/476 |

FOREIGN PATENT DOCUMENTS

| EP | 0427519 | 5/1991 | ............ A61K/9/22 |
| EP | 0548448 | 6/1993 | ............ A61K/9/50 |
| EP | 0585688 | 3/1994 | ............ C08L/89/00 |
| EP | 0621032 | 10/1994 | ............ A61K/9/28 |
| GB | 2245492 | 1/1992 | ............ A61K/9/22 |
| WO | 8300435 | 2/1983 | ............ A61K/9/32 |

* cited by examiner

*Primary Examiner*—James M. Spear
(74) *Attorney, Agent, or Firm*—Davidson, Davidson & Kappel, LLC

(57) ABSTRACT

A controlled release tablet for oral administration is disclosed which has a tablet core including an insoluble therapeutically active agent having an aqueous solubility of less than or equal to about 5 mg/ml in a sufficient amount to render a therapeutic effect. The core provides rapid release of said therapeutically active agent upon exposure to aqueous solutions. The tablet core is coated with a controlled release coating permitting sustained release of said therapeutically active agent when said coated tablet is exposed to aqueous solutions.

27 Claims, 6 Drawing Sheets

IMMEDIATE RELEASE TABLET CORES OF INSOLUBLE DRUGS HAVING SUSTAINED-RELEASE COATING

This application is a continuation of U.S. patent application Ser. No. 09/505,935, filed on Feb. 14, 2000, now U.S. Pat. No. 6,210,714 which is a continuation of U.S. patent application Ser. No. 08/467,575, filed Jun. 6, 1995, now U.S. Pat. No. 6,024,982, issued Feb. 15, 2000, which is a divisional of U.S. patent application Ser. No. 08/156,460, filed Nov. 23, 1993, now U.S. Pat. No. 5,500,227, issued Mar. 19, 1996, the disclosures of which are hereby incorporated by reference.

BACKGROUND OF THE INVENTION

The maximum time of effectiveness of many oral dosage forms is only a few hours. In order to maximize patient compliance, it is considered very desirable to reduce the frequency of dosing, thereby reducing the number dosage forms (e.g., tablets, etc.) a patient must take in order to attain effective therapy.

Sustained release formulations for drugs have become increasingly available. This is true especially when the particular drug is relatively soluble. Various formulation techniques have been used for providing a sustained release formulation of soluble drugs. In many such formulations, a drug-containing particle is coated with a coating layer or is dispersed within a continuous matrix such as a polymeric matrix. The coating layer or the matrix comprises a relatively insoluble material or materials, and the release of the drug is controlled by means of the resistance of the coating layer or matrix against the diffusion of the drug therethrough. The release of the drug from such formulations is driven, e.g., by the gradient of the drug concentration resulting from penetration of, e.g., gastric fluid, by diffusion into the formulation.

The task of preparing controlled release formulations of relatively insoluble drugs has proven to be more difficult, however. Examples of such relatively insoluble drugs include acetaminophen, naproxen and indomethacin.

In part because the bioavailability of relatively insoluble drugs is highly dependent on the particle size of the drug or its specific surface area, much of the prior art directed to the provision of controlled release dosage forms for relatively insoluble drugs involves the use of pellets, beads or spheres having a relatively small particle size.

For example, U.S. Pat. No. 4,840,799 (Appelgren, et al.) is related to the preparation of rapidly disintegrating core granulates of slightly soluble drugs (solubility of <1000 mg/l) wherein the drug in particulate form is coated with a layer of an emulsifier/tensile having the same HLB-value as the solubility of the drug. The product is said to provide high bioavailability via the rapid disintegration and release of the drug at a suitable location along the gastrointestinal tract.

With regard to controlled (slow) release formulations, in U.S. Pat. No. 4,752,470 (Mehta), a controlled release indomethacin formulation is described wherein coated pellets of indomethacin of only one type are described. The pellet is said to release indomethacin in both immediate and sustained release form. The pellet consists of a non-pareil bead which supports indomethacin and a binder agent, which is then coated with a mixture of hydroxypropyl cellulose, ethyl cellulose and a plasticizer. The loaded pellets are preferably composed of 2–10% by weight binder, and about 5–30% by weight indomethacin. The pellets are then coated with 0.5–10% by weight of the mixture of hydroxypropyl cellulose and ethyl cellulose. The ratio of ethyl cellulose to hydroxypropyl cellulose depends upon the desired controlled release characteristics.

U.S. Pat. No. 5,133,974 (Paradissis, et al.) describes an extended release formulation which consists of a mixture of 0–50% immediate release particles containing a drug, an inert substrate and binder coated with talc, and up to 100% of an extended release particle comprising the immediate release particle coated with a dissolution modifying system containing plasticizers and a film forming agent. Optionally, additionally a drug is included in the coating.

On the other hand, U.S. Pat. No. 4,892,741 (Ohm, et al.) describes a coated tablet consisting of a core which contains a dihydropyridine having a low aqueous solubility (e.g., nifedipine, nitrendipine, nimodipine and nisoldipine) in rapid-release form and a coating around the core containing a dihydropyridine in slow-release form. The rapid-release core preferably contains the active compound in amorphous form or in a finely grounded or micronized crystalline form. The granules for the coating of the tablet contain 10–99% of hydrophilic gel-forming polymers together with the drug. The coating is carried out on a press coater.

U.S. Pat. No. 3,184,386 describes tablets having a rapid-release preparation in the outer coating. The core primarily has a function of not allowing the surface of the outer coating containing the drug to become too small for release purposes. However, the core does not contain drug in rapid-release form. Both the central coat and the core are also described in the examples as slow-release forms of highly soluble active compounds. U.S. Pat. No. 3,558,768 also describes coated tablets which contain drug in the slow-release form both in the core and in the coating.

It has been found that, when attempting to prepare controlled-release tablets of an insoluble drug contained within a controlled release matrix, such formulations suffer from unacceptable batch to batch and dosage unit to dosage unit dissolution variability which would in turn result in such products not being commercially viable.

SUMMARY OF THE INVENTION

It is an object of the present invention to provide a controlled release formulation of a relatively insoluble drug which displays acceptable batch-to-batch and dosage unit to dosage unit dissolution reproducibility.

It is another object of the present invention to provide a controlled release tablet of a relatively insoluble drug which provides a reproducible in-vitro dissolution profile on a batch-to-batch basis.

It is another object of the present invention to provide a method of preparing a controlled release tablet of a relatively insoluble drug which can be manufactured with relative ease.

The above objects and others are achieved by virtue of the present invention, which relates to a controlled release tablet for oral administration, comprising a core including a therapeutically active agent (drug) having a solubility of less than or equal to about 5 mg/ml in an amount sufficient to render a therapeutic effect, the core providing immediate release of said therapeutically active agent upon exposure to aqueous solution, the immediate release core being coated with a sustained release coating.

The present invention further relates to a method for preparing a oral controlled release formulation of an insoluble drug, comprising coating an immediate release tablet core including a therapeutically active agent in an amount sufficient to render a therapeutic effect, the therapeutically active agent having a solubility of less than or equal to about 5 mg/ml in an amount sufficient to render a therapeutic effect, with a sustained release coating having a sufficient thickness to cause the therapeutically active agent to be release slowly when exposed to an aqueous solution.

In certain preferred embodiments, the sustained release coating comprises an aqueous dispersion of a plasticized hydrophobic polymer selected from the group consisting of ethylcellulose, a polymer or copolymer of acrylates or methacrylates, and a mixture thereof to a weight gain from about 3 to about 20 percent. Preferably, the coating tablet cores of the embodiments are cured at a temperature above the glass transition temperature of the plasticized coating and at a requisite relative humidity until an endpoint is reached at which the cured coated tablet provides a stable dissolution profile. The endpoint is determined by comparing the dissolution profile of the coated tablet immediately after curing to the dissolution profile of the coated tablet after exposure to accelerated storage conditions of three months at a temperature from about 37° C. to about 40° C. and a relative humidity from about 75% to about 80%.

The present invention also relates to a sustained release tablet for oral administration, comprising an immediate release tablet core including from about 300 mg to about 500 mg acetaminophen, and a therapeutically effective amount of an analgesic agent selected from hydromorphone, oxycodone, dihydrocodeine, codeine, dihydromorphine, morphine, buprenorphine, other opioids, salts of any of the foregoing, and mixtures of any of the foregoing, the tablet core being coated with a sufficient amount of a hydrophobic polymer such that the acetaminophen and the analgesic agent are released from the coated tablet over an extended period of time. The immediate release tablet core providing the dissolution of not less than 75% of the acetaminophen in 45 minutes when said tablet core is placed in 900 ml 0.1 N hydrochloric acid. The present invention is further related to a sustained release oral solid dosage form comprising an immediate release tablet core comprising an insoluble therapeutically active agent having a solubility of less than or equal to about 5 mg/ml and a soluble therapeutically active agent which is highly soluble in water relative to said insoluble therapeutically active agent, the immediate release tablet core being capable of releasing not less than 75% of said insoluble and said soluble therapeutically active agents in 45 minutes when placed in 900 ml 0.1 N hydrochloric acid, and an effective amount of a sustained release coating formed over said tablet core. The coating, in certain preferred embodiments, comprises an aqueous dispersion of a plasticized hydrophobic polymer selected from the group consisting of ethylcellulose, a polymer or copolymer of acrylates or methacrylates, and a mixture thereof to a weight gain from about 3 to about 20 percent. In certain preferred embodiments, the insoluble therapeutically active agent is acetaminophen and said soluble therapeutically active agent is selected from the group consisting of hydromorphone, oxycodone, dihydrocodeine, codeine, dihydromorphine, morphine, buprenorphine, salts of any of the foregoing, and mixtures of any of the foregoing.

By "immediate release core", it is meant for purposes of the present invention that the tablet core containing the therapeutically active agent(s) meets the disintegration and/or dissolution requirements for immediate release tablets of the particular therapeutically active agent(s) included in the tablet core, as set forth in the USP XXII, 1990 (The United States Pharmacopeia).

By "sustained release", it is meant for purposes of the present invention that the release of the therapeutically active agent occurs such that blood levels are maintained within a desired therapeutic range over an extended period of time, e.g., at least about 8 and preferably from about 12 to about 24 hours. The "dissolution requirements" and "disintegration requirements" referred to above are conducted using the equipment and tests specified in the USP XXII and conducted pursuant to the individual Official Monographs of USP XXII for the particular therapeutically active agent(s) included in the tablet core.

BRIEF DESCRIPTION OF THE DRAWINGS

The following drawings are illustrative of embodiments of the invention and are not meant to limit the scope of the invention as encompassed by the claims.

DETAILED DESCRIPTION

Figure 1:
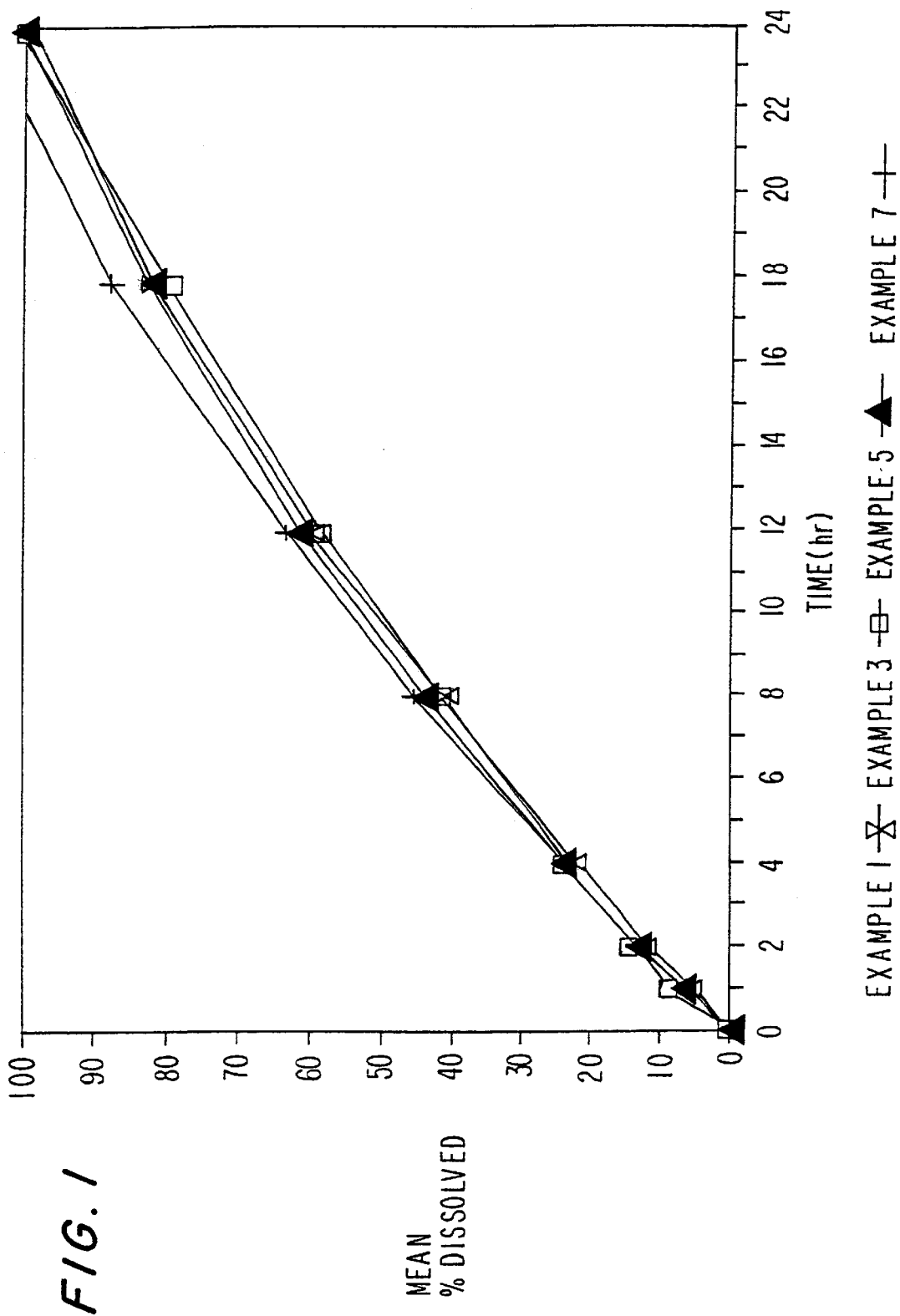
FIG. 1 is a graphical representation of the dissolution obtained for Examples 1, 3, 5 and 7.

Once orally administered, solid dosage forms containing one or more drugs must allow the drug(s) to dissolve in the gastrointestinal tract in order for the drug to be absorbed. The rate and extent of the dissolution of a drug in the gastrointestinal tract can greatly influence the rate and extent of absorption of the drug. It is especially important that the dosage form have a high bioavailability of the drug in order to (1) reduce the total amount of drug which must be administered to obtain a therapeutic effect, and (2) decrease the biological variability in the drug levels in the circulation.

The solubility of the solid drug itself can also greatly influence its absorption in the gastrointestinal tract and its bioavailability. Compounds with an aqueous solubility of greater than 1% w/v are not expected to present dissolution-related absorption problems. See, e.g., *Pharmaceutical Dosage Forms—Tablets*, Vol. 1, page 13, Edited by H. Lieberman, Marcel Dekker, Inc. ©1980.

While certain highly insoluble drugs may dissolve rapidly in the gastrointestinal tract if provided, e.g., in very fine particulate form and in small doses, it is often the case that such tactics are not possible. This may be due, for example, to the necessary dosage of the drug required to obtain a desired therapeutic effect. In such cases where the particle size or dosage does not in and of itself provide the necessary rate and extent of dissolution, efforts must be made through pharmaceutical formulation considerations to alter the "normal" dissolution of the drug in order to provide an acceptable rate and extent of dissolution in the gastrointestinal tract.

The problems associated with developing a reproducible dissolution profile for insoluble drugs has been recognized, e.g., by the United States Food and Drug Administration (FDA). For example, this Agency has for years recognized the difficulty in developing a regulatory policy, based on solid pharmaceutic principles, for scaling-up solid oral dosage form batch sizes. While FDA generally allows firms to employ a minimum batch size of 100,000 units with the provision for up-scaling by 10 fold on the basis of similar dissolution profiles, and the routine use of a batch size of 10% of the proposed production batch, or 100,000 units, whichever is greater, separate procedures have been proposed for regulating scale-up of dosage forms for very soluble drugs, drugs having a narrow therapeutic index, and cases where different equipment designs and operating principles are to be employed in the production batch size. For very soluble drugs, a dissolution profile is all that would be required. Where equipment of different design or operating principle is employed, an in-vivo bioavailability study might be required. Quantitative adjustment of a particular dosage form within the above ranges is considered by FDA to be a relatively minor change.

However, FDA has recognized that changes in particle size, surface area and/or intrinsic dissolution can have significant effects in the specifications of the final product, and that end process testing requirements need to be determined on the basis of the bioavailability problem potential of the drug. See, e.g., FDA/AAPS Workshop Report, "Scale-up Of Immediate Release Oral Solid Dosage Forms", December 1991 by Skelly, et al. Thus, for drug substances with an aqueous solubility of ≦5 mg/ml, a change greater than 10% in mean particle size (distribution remaining approximately the same), surface area, or intrinsic dissolution rate, may be considered to represent a major change which might require in vivo bioavailability study. Furthermore, it is recognized that for very slightly soluble drugs with high permeability (e.g., an extent of absorption into the intestinal tract greater than 90% in the absence of luminal instability), dissolution is likely the critical variable controlling drug absorption.

Drugs with a dose/solubility volume of greater than or equal to 5 mg/ml are defined as high solubility drugs. For such drugs, dissolution of 85% in 30 minutes, in 900 ml of 0.1 N HCl may be all that is required.

For high permeability-low solubility or high solubility-low permeability drugs, a dissolution profile (15, 30, 45, 60, 120, 180 minutes (or until either 90% is dissolved, or an asymptote is reached)) in media of differing pH, with a 95% confidence interval encompassing the "reference batch" (previous market formulation batch having known bioavailability or defined clinical efficacy), is required. Profiles should be obtained in water, 0.1 N HCl, and USP buffer media at pH 4–8, e.g., pH 4.5, 6.5 and 7.5. A surfactant may be used if it was in the original application, or can be otherwise justified.

Because of the expected sensitivity of absorption to in vivo dissolution, in vivo data are required for low permeability, low solubility drugs.

Pursuant to the present invention, it has been surprisingly discovered that controlled release formulations of insoluble drugs can be prepared, which formulations provide the requisite batch-to-batch reproducibility and scale-up reproducibility with regard to in-vitro dissolution, via overcoating immediate release tablet cores containing the insoluble drug with a controlled release film coating. This procedure provides relative ease with regard to process steps and formulation requirements and costs compared to other attempts at providing controlled release dosage forms of such drugs.

Insoluble drugs which may be used in conjunction with the present invention include, therefore, those drugs which have an aqueous solubility of ≦5 mg/ml. Such insoluble drugs include, for example, acetaminophen (APAP), naproxen, theophylline, nifedipine and indomethacin.

In the present invention, the insoluble drug(s) is incorporated into a tablet core which is designed to provide immediate dissolution of the drug upon exposure of the tablet core to aqueous solutions, including in vitro dissolution solutions and gastrointestinal fluid.

In certain preferred embodiments of the present invention, the immediate release tablet core is obtained by mixing the required quantity of insoluble drug having a necessary particle size with other materials usually included in tablets, such as diluents, lubricants, binders, etc. In certain embodiments, for example, it may be necessary to include one or more disintegrants in the tablet core. After the insoluble drug is mixed with the additional tableting ingredients, the mixture is then tableted on a suitable tableting machine.

The resultant immediate release tablet core should meet the dissolution requirements for immediate release tablets of the therapeutically active agent as set forth in USP XXII. For example, when the insoluble drug is acetaminophen, the tablet core preferably dissolves in 900 ml of pH 5.8 phosphate buffer in 30 minutes.

The immediate release tablet cores containing the insoluble drug(s) are preferably film coated with a material that permits release of the insoluble drug at a controlled rate in an aqueous medium. The film coat is preferably chosen so as to achieve, in combination with the other ingredients, an in vitro dissolution rate for a 12 or 24-hour dosage form, when measured by the USP Paddle Method at 100 rpm in 900 ml aqueous buffer, substantially independent of pH, at 37° C. between 12.5 and 42.5% (by wt) drug released after 1 hour, between 25 and 56% (by wt) drug released after 2 hours, between 45 and 75% (by wt) drug released after 4 hours and between 55 and 85% (by wt) drug released after 6 hours. USP Paddle Method is the Paddle Method described, e.g., in U.S. Pharmacopoeia XXII (1990).

In the present specification, "substantially independent of pH" means that the difference, at any given time, between the amount of drug released at, e.g., pH 1.6, and the amount released at any other pH, e.g., pH 7.2 (when measured in vitro using the USP Paddle Method at 100 rpm in 900 ml aqueous buffer), is 10% (by weight) or less, the amounts released being, in all cases, a mean of at least three experiments.

The film coat will generally include a water insoluble material such as a wax or a wax-like substance, fatty alcohols, shellac, zein, hydrogenated vegetable oils, water insoluble celluloses, polymers of acrylic and/or methacrylic acid, and any other slowly digestible or dispersible solids known in the art. The coating formulations of the present invention should be capable of producing a strong, continuous film that is smooth and elegant, capable of supporting pigments and other coating additives, non-toxic, inert, and tack-free. Generally, the film coat is applied to the tablet core to achieve a weight gain level from about 2 to about 25 percent. However, the film coat may be lesser or greater depending upon the physical properties of the insoluble drug(s) included in the formulation and the desired release rate. The solvent for the hydrophobic coating material may be organic or aqueous.

In a preferred embodiment, the film coating of the present invention is obtained via the use of an aqueous dispersion of a hydrophobic polymer. Preferably, the hydrophobic polymer is selected from (i) a water insoluble cellulosic polymer, such as an alkylcellulose, preferably ethylcellulose; (ii) an acrylic polymer; or (iii) mixtures thereof; and cured at conditions of temperature and relative humidity greater than ambient conditions until a stabilized dissolution profile substantially unaffected by exposure to accelerated storage conditions is obtained. By the phrase "accelerated storage conditions" it is meant, e.g., storage conditions of elevated temperature and/or elevated relative humidity. For the purposes of the present invention, "accelerated storage conditions" is defined as storage conditions to which the final drug formulation is subjected for the purpose of obtaining regulatory approval (e.g., FDA approval in the U.S.) and an expiration date.

For example, a generally accepted test employed in FDA guidelines relates to the storage of a drug product (e.g., in its container and package) at 75% Relative Humidity (RH) at 40° C. If the product holds up for, e.g., three months under these conditions (chemical stability, dissolution, and physical characteristics), then the drug product will be accorded, e.g., a two year expiration date. Other generally accepted accelerated tests include those where the drug product is subjected to 80% RH and 37° C. for, e.g., one month or longer, and preferably three months.

In other preferred embodiments of the present invention, the hydrophobic material comprising the controlled release coating is an acrylic polymer. Any acrylic polymer which is pharmaceutically acceptable can be used for the purposes of the present invention. The acrylic polymers may be cationic, anionic or non-ionic polymers and may be acrylates, methacrylates, formed of methacrylic acid or methacrylic acid esters. These polymers can be synthesized, as indicated above, to be cationic, anionic or non-ionic, which then renders the polymers that would be pH dependent and consequently soluble in, or resistant to solutions over a wide range in pH. The most available of the acrylic polymers for the purposes of the present invention are those that are marketed under the trade name "EUDRAGIT" and are available from Rohm Pharma. GmbH, Weiterstat, West Germany.

Examples of suitable acrylic polymers include but are not limited to acrylic acid and methacrylic acid copolymers, methacrylic acid copolymers, methyl methacrylate copolymers, ethoxyethyl methacrylates, cynaoethyl methacrylate, methyl methacrylate, copolymers, methacrylic acid copolymers, methyl methacrylate copolymers, methyl methacrylate copolymers, methyl methacrylate copolymers, methacrylic acid copolymer, aminoalkyl methacrylate copolymer, methacrylic acid copolymers, methyl methacrylate copolymers, poly(acrylic acid), poly (methacrylic acid, methacrylic acid alkylamine copolymer, poly(methyl methacrylate), poly(methacrylic acid) (anhydride), methyl methacrylate, polymethacrylate, methyl methacrylate copolymer, poly(methyl methacrylate), poly (methyl methacrylate) copolymer, polyacrylamide, aminoalkyl methacrylate copolymer, poly(methacrylic acid anhydride), and glycidyl methacrylate copolymers. This list is not meant to be exclusive.

Preferably, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups. In order to obtain a desirable dissolution profile for a given therapeutically active agent, such as that detailed above, it may be necessary to incorporate two or more ammonio methacrylate copolymers having differing physical properties. For example, it is known that by changing the molar ratio of the quaternary ammonium groups to the neutral (meth)acrylic esters, the permeability properties of the resultant coating can be modified.

The inclusion of an effective amount of a plasticizer in the aqueous dispersion of hydrophobic polymer will further improve the physical properties of the film. For example, because ethylcellulose has a relatively high glass transition temperature and does not form flexible films under normal coating conditions, it is necessary to plasticize the ethylcellulose before using the same as a coating material.

The plasticization of the ethylcellulose may be accomplished either by so-called "internal plasticization" and "external plasticization." The suitability of a plasticizer depends on its affinity or solvating power for the polymer and its effectiveness at interfering with polymer-polymer attachments. Such activity imparts the desired flexibility by relieving molecular rigidity. Generally, the amount of plasticizer included in a coating solution is based on the concentration of the film-former, e.g., most often from about 1 to about 50 percent by weight of the film-former. Concentration of the plasticizer, however, can only be properly determined after careful experimentation with the particular coating solution and method of application. Most preferably, about 20% plasticizer is included in the aqueous dispersion of acrylic polymer.

An important parameter in the determination of a suitable plasticizer for a polymer is related to the glass transition temperature (Tg) of the polymer. The glass transition temperature is related to the temperature or temperature range where there is a fundamental change in the physical properties of the polymer. This change does not reflect a change in state, but rather a change in the macromolecular mobility of the polymer.

Below the Tg, the polymer chain mobility is severely restricted. Thus, for a given polymer, if its Tg is above room temperature, the polymer will behave as a glass, being hard, non-pliable and rather brittle, properties which could be somewhat restrictive in film coating since the coated dosage form may be subjected to a certain amount of external stress.

Incorporation of suitable plasticizers into the polymer matrix effectively reduces the Tg, so that under ambient conditions the films are softer, more pliable and often stronger, and thus better able to resist mechanical stress.

Other aspects of suitable plasticizers include the ability of the plasticizer to act as a good "swelling agent" for the ethylcellulose, and the solubility profile of the plasticizer in water.

Examples of suitable plasticizers for ethylcellulose include dibutyl sebacate, diethyl phthalate, triethyl citrate and tibutyl citrate, although it is possible that other plasticizers (such as acetylated monoglycerides, phthalate esters, castor oil, etc.) may be used. Triethyl citrate is an especially preferred plasticizer for the aqueous dispersions of ethyl cellulose of the present invention.

Examples of suitable plasticizers for the acrylic polymers of the present invention include, but are not limited to citric acid esters such as triethyl citrate NF XVI, tributyl citrate, dibutyl phthalate, and possibly 1,2-propylene glycol. Other plasticizers which have proved to be suitable for enhancing the elasticity of the films formed from acrylic films such as Eudragit® RL/RS lacquer solutions include polyethylene glycols, propylene glycol, diethyl phthalate, castor oil, and triacetin. Triethyl citrate is an especially preferred plasticizer for the aqueous dispersions of ethyl cellulose of the present invention.

It has further been found that the addition of a small amount of talc reduces the tendency of the aqueous dispersion to stick during processing, and acts as a polishing agent.

One commercially-available aqueous dispersion of ethylcellulose is Aquacoat® (FMC Corp., Philadelphia, Pa., U.S.A.). Aquacoat® is prepared by dissolving the ethylcellulose in a water-immiscible organic solvent and then emulsifying the same in water in the presence of a surfactant and a stabilizer. After homogenization to generate submicron droplets, the organic solvent is evaporated under vacuum to form a pseudolatex. The plasticizer is not incorporated in the pseudolatex during the manufacturing phase. Thus, prior to using the same as a coating, it is necessary to intimately mix the Aquacoat® with a suitable plasticizer prior to use.

Another aqueous dispersion of ethylcellulose is commercially available as Surelease® (Colorcon, Inc., West Point, Pa., U.S.A.). This product is prepared by incorporating plasticizer into the dispersion during the manufacturing process. A hot melt of a polymer, plasticizer (dibutyl sebacate), and stabilizer (oleic acid) is prepared as a homogeneous mixture, which is then diluted with an alkaline solution to obtain an aqueous dispersion which can be applied directly onto substrates.

In one preferred embodiment, the acrylic coating is an acrylic resin lacquers used in the form of an aqueous dispersion, such as that which is commercially available from Rohm Pharma under the Tradename Eudragit®. In further preferred embodiments, the acrylic coating comprises a mixture of two acrylic resin lacquers commercially available from Rohm Pharma under the Tradenames Eudragit® RL 30 D and Eudragit® RS 30 D, respectively. Eudragit® RL 30 D and Eudragit® RS 30 D are copolymers of acrylic and methacrylic esters with a low content of quaternary ammonium groups, the molar ratio of ammonium groups to the remaining neutral (meth)acrylic esters being 1:20 in Eudragit® RL 30 D and 1:40 in Eudragit® RS 30 D. The mean molecular weight is about 150,000. The code designations RL (high permeability) and RS (low permeability) refer to the permeability properties of these agents. Eudragit® RL/RS mixtures are insoluble in water and in digestive fluids. However, coatings formed from the same are swellable and permeable in aqueous solutions and digestive fluids.

The Eudragit® RL/RS dispersions of the present invention may be mixed together in any desired ratio in order to ultimately obtain a controlled release formulation having a desirable dissolution profile. Desirable controlled release formulations may be obtained, for instance, from a retardant coating derived from 100% Eudragit® RL; 50% Eudragit® RL, 50% Eudragit® RS; and 10% Eudragit® RL, 90% Eudragit® RS.

The stabilized controlled release formulations of the present invention slowly release the insoluble drug(s), e.g., when ingested and exposed to gastric fluids, and then to intestinal fluids. The controlled release profile of the formulations of the invention can be altered, for example, by varying the amount of overcoating with the aqueous dispersion of hydrophobic polymer, altering the manner in which the plasticizer is added to the aqueous dispersion of hydrophobic polymer, by varying the amount of plasticizer relative to hydrophobic polymer, by the inclusion of additional ingredients or excipients, by altering the method of manufacture, etc.

The coating solutions of the present invention may contain, in addition to the film-former, plasticizer, and solvent system (i.e., preferably water but also encompassing organic solvents), a colorant to provide elegance and product distinction. Color may be added to the solution of the therapeutically active agent instead, or in addition to the aqueous dispersion of hydrophobic polymer. For example, color can be added to Aquacoat® via the use of alcohol or propylene glycol based color dispersions, milled aluminum lakes and opacifiers such as titanium dioxide by adding color with shear to the water soluble polymer solution and then using low shear to the plasticized Aquacoat®. Alternatively, any suitable method of providing color to the formulations of the present invention may be used. Suitable ingredients for providing color to the formulation when an aqueous dispersion of an acrylic polymer is used include titanium dioxide and color pigments, such as iron oxide pigments.

The plasticized aqueous dispersion of hydrophobic polymer may be applied onto the tablet core comprising the insoluble drug by spraying, using any suitable spray equipment known in the art. In a preferred method, a Wurster fluidized-bed system is used in which an air jet, injected from underneath, fluidizes the core material and effects drying while the acrylic polymer coating is sprayed on. A sufficient amount of the aqueous dispersion of hydrophobic polymer to obtain a predetermined controlled release of the therapeutically active agent when the coated substrate is exposed to aqueous solutions, e.g. gastric fluid, is preferably applied, taking into account the physical characteristics of the therapeutically active agent, the manner of incorporation of the plasticizer, etc. After coating with the hydrophobic polymer, a further overcoat of a film-former, such as hydroxypropylmethylcellulose (e.g., Opadry®), is optionally applied to the tablets. This overcoat is provided, if at all, in order to substantially reduce agglomeration of the tablets.

Next, the coated tablets are cured in order to obtain a stabilized release rate of the therapeutically active agent.

To date, attempts to prepare stable controlled release pharmaceutical formulations using aqueous dispersions of hydrophobic polymers have been unsuccessful due to stability problems. In particular, when coating these pharmaceutical forms using aqueous polymeric dispersions to obtain a desired release profile of the active drug(s) over several hours or longer, it is known in the art that the dissolution release profile changes on ageing.

This problem has been overcome by curing the coated tablet at a temperature greater than the glass transition temperature of the aqueous dispersion of plasticized hydrophobic polymer and at a necessary relative humidity until an endpoint is reached at which said substrate attains a dissolution profile which is substantially unaffected by exposure to accelerated storage conditions, e.g., of about 37°–40° C. and about 75–80% relative humidity for three months or longer. In other words, the cured coated tablet will provide a stable dissolution profile when comparing the in vitro dissolution of the therapeutically active agent immediately after curing to the in vitro dissolution of the therapeutically active agent after exposing the cured coated substrate to accelerated conditions of three months at from about 37° C. to about 40° C. and from about 75% to about 80% pH. By "stable" it is meant that the in vitro dissolution falls within acceptable limits in comparison to the dissolution profile of the coated cured substrate immediately after curing, the acceptable limits being determined by a regulatory agency such as the U.S. F.D.A.

In the embodiment of the present invention wherein an aqueous dispersion of ethylcellulose is used as the controlled release coating, wherein the curing step is accomplished by subjecting the coated substrate to greater than normal, ambient (i.e., room) temperature and relative humidity and continuing the curing until an endpoint is reached at which the coated beads attain a dissolution profile which is substantially unaffected by further exposure to storage conditions of elevated temperature and/or humidity. More particularly, the coated substrates of the present invention should be cured at a temperature greater than the glass transition temperature of the coating solution (i.e., ethylcellulose) and at a greater than ambient humidity.

In preferred embodiments of the present invention, the stabilized product derived from an aqueous dispersion of ethylcellulose is obtained by subjecting the coated substrate to oven curing at the aforementioned temperature/humidity levels for the required time period, the optimum values for temperature, humidity and time for the particular formulation being determined experimentally. In certain preferred embodiments, the stabilized product coated with an aqueous dispersion of ethylcellulose is obtained via an oven curing conducted at a temperature of about 60° C. and a relative humidity from about 60% to about 100% for a time period from about 48 to about 72 hours.

Traditionally, curing has been carried out for Eudragit® coated formulations, if at all, via a fluid bed at 45° C. for 2 hours after application. Such a standard curing is recommended by Rohm Pharma because it is above the glass transition temperature (Tg) of Eudragit® RS 30 D plasticized with triethylcitrate at a 20% level of solids. However, this recommended curing does not stabilize the dissolution profile of the formulation upon exposure to accelerated storage conditions.

This problem is overcome in the embodiment of the present invention wherein the aqueous dispersion of hydrophobic polymer comprises an aqueous dispersion of an acrylic polymer such as Eudragit®, wherein the stabilized product is obtained via an oven curing conducted at a temperature greater than the Tg of the coating formulation and continuing the curing until an endpoint is reached at which the coated formulation. In other words, the cured coated tablet will provide a stable dissolution profile when comparing the in vitro dissolution of the therapeutically active agent immediately after curing to the in vitro dissolution of the therapeutically active agent after exposing the cured coated substrate to accelerated conditions of three months at from about 37° C. to about 40° C. and from about 75% to about 80% RH. By "stable" it is meant that the in vitro dissolution falls within acceptable limits in comparison to the dissolution profile of the coated cured substrate immediately after curing. The acceptable limits being determined by a regulatory agency such as the U.S. F.D.A.

In preferred embodiments of the present invention directed to the acrylic coating, the stabilized product is obtained by subjecting the coated substrate to oven curing at a temperature above the Tg of the plasticized acrylic polymer for the required time period, the optimum values for temperature and time for the particular formulation being determined experimentally. In certain embodiments of the present invention, the stabilized product is obtained via an oven curing conducted at a temperature of about 45° C. for a time period from about 24 to about 48 hours. It is also contemplated that certain products coated with the controlled release coating of the present invention may require a curing time longer than 48 hours, e.g. 60 hours or more.

One skilled in the art will recognize that necessary curing conditions will vary, depending upon (among other things) the particular therapeutically active agent included in the formulation, the size of the substrate, the thickness of the coating, the percentage of hydrophobic polymer included in the aqueous dispersion, the presence and amount of additional rate-controlling agents included in the aqueous dispersion of hydrophobic polymer. The necessary time period to cure to the stabilized end point may also be affected by the above variants and others. Such curing conditions are contemplated to be within the scope of the present invention and the appended claims.

The release of the therapeutically active agent from the controlled release formulation of the present invention can be further influenced, i.e., adjusted to a desired rate, by the addition of one or more release-modifying agents included in the coating. The amount of such release-modifying agents included in the coating will depend upon the release rate required and the solubility characteristics of the agent selected, among other things.

For example, the controlled release coating may comprise a water soluble material(s) in addition to the hydrophobic polymer. The ratio of hydrophobic polymer to water soluble material is determined by, among other factors, the release rate required and the solubility characteristics of the materials selected. Suitable water soluble materials include hydrophilic polymers.

Also, cellulose ethers and protein-derived materials can be included in the controlled release coating to modify the release characteristics thereof. These materials include, but are not limited to cellulose derivatives, including but not limited to hydroxyalkyl celluloses and carboxyalkyl celluloses, such as hydroxypropyl-cellulose, hydroxypropylmethylcellulose, methoxypropyl cellulose, hydroxyethyl cellulose, and other derivatives known to those skilled in the art. Each of these cellulosic derivatives are available in a range of molecular weights and viscosities, etc., and the particular cellulosic derivative to be utilized in the present invention may be chosen as the need arises. Semipermeable polymers may also be used. Such polymers include, for example, cellulose acylate, cellulose diacylate, cellulose triacylate, cellulose acetate, cellulose diacetate, cellulose triacetate, beta-glycan acetate, acetaldehyde dimethyl acetate, cellulose acetate ethyl carbamate, polyamide, polyurethane, sulfonated polystyrene, cellulose acetate phthalate, cellulose acetate methyl carbamate, cellulose acetate succinate, cellulose acetate dimethylaminoacetate, cellulose acetate chloracetate, cellulose dipalmitate, cellulose dioctanoate, cellulose dicaprylate, cellulose dipentanlate, cellulose acetate valerate, cellulose acetate p-toluenesulfonate, cellulose acetate butyrate, and other semi-permeable polymers such as those described in U.S. Pat. No. 4,285,987 (hereby incorporated by reference), selectively permeable polymers formed by the coprecipitation of a polycation and a polyanion as disclosed in U.S. Pat. Nos. 3,173,876, 3,276,586; 3,541,005; 3,541,006 and 3,546,142 (hereby incorporated by reference).

In addition, a water-soluble polydextrose may be used. A water-soluble polydextrose is defined for the purposes of the present invention as a polydextrose that dissolves to a level of at least about 1% (W/W) in water at 25° C. Also, synthetic water-soluble polymers may be used, such as polyvinylpyrrolidone, cross-linked polyvinylpyrrolidone, polyethylene oxide, etc., and polysaccharides, e.g., pullulan, dextran, etc.

The controlled release coatings of the present invention can also include release-modifying agents such as cellulose acetate phthalate, such as those disclosed in U.S. Pat. No. 2,196,768, herein incorporated by reference. Other suitable release-controlling agents which may be included in the controlled release coating of the present invention include shellac, zein, hydroxypropylmethyl cellulose phthalate, sandarac, modified shellac, etc.

The release-modifying agents of the present invention also encompass erosion-promoting agents such as starch (including, but not limited to corn starch, rice starch, a starch, carboxymethyl starch, potato starch, and other vegetable starches), modified starch, and starch derivatives. This category is also intended to include other erosion-promoting agents such as gums (e.g., xanthan gum, alginic acid, other alginates, bentonite, veegum, agar, guar, locust bean gum, gum arabic, quince psyllium, flax seed, okra gum, arabinoglactin, pectin, tragacanth, scleroglucan, dextran, amylose, amylopectin, dextrin, etc., cross-linked polyvinylpyrrolidone, ion-exchange resins, such as potassium polymethacrylate, carrageenan, kappa-carrageenan, lambdacarrageenan, gum karaya, biosynthetic gum, etc.).

The controlled release coatings of the present invention can also include materials useful for making microporous lamina in the environment of use. Materials useful for making the microporous lamina include polycarbonates comprised of linear polyesters of carbonic acid in which carbonate groups reoccur in the polymer chain, microporous materials prepared by the phosgenation of a dihydroxyl aromatic such as bisphenol, a microporous poly (vinylchloride), microporous polyamides such as polyhexamethylene adipamide, microporous modacrylic copolymers including those formed from poly(vinychloride) and acrylonitrile, microporous styreneacrylic and its copolymers, porous polysulfones characterized by diphenylene sulfone in a linear chain thereof, halogenated poly (vinylidene), polychloroethers, acetal polymers, polyesters prepared by esterification of a dicarboxylic acid or anhydride with an alkylene polyol, poly(alkylenesulfides), phenolics, polyesters, microporous polysaccharides having substituted anhydroglucose units exhibiting a decreased permeability to the passage of water and biological fluids, asymmetric porous polymers, cross-linked olefin polymers, hydrophobic or hydrophilic microporous homopolymers, copolymers or interpolymers having a reduced bulk density, and materials described in U.S. Pat. Nos. 3,595,752; 3,643, 178; 3,654,066; 3,709,774; 3,718,532; 3,803,601; 3,852, 224; 3,852,388; and 3,853,601 (all of which are hereby incorporated by reference); in British Pat. No. 1,126,849; and in Chem. Abst. Vol. 71, 427F, 22573F, 1969.

Additional microporous materials for forming microporous lamina include poly(urethane), cross-linked chain-extended poly(urethane), poly(imides), poly (benzimidazole), collodion, regenerated proteins, semi-solid cross-linked poly(vinylpyrrolidone), microporous materials prepared by diffusion of multivalent cations into polyelectrolyte sols, microporous derivatives of poly(styrene) such as poly(sodium-styrenesulfonate), poly(vinyl benzyl trimethyl-ammonium chloride), microporous cellulosic acrylates and the like microporous polymers such as those described in U.S. Pat. Nos. 3,524,753; 3,565,259; 3,276, 589; 3,541,055; 3,541,006; 3,546,142; 3,615,024; 3,646, 178, and 3,852,224 (all of which are hereby incorporated by reference). Pore-formers useful for forming the microporous lamina in the environment of use include solids and pore-forming liquids.

The term pore-former as used herein also embraces micropath formers, and removal of the pore and/or pore-former leads to both embodiments. In the expression pore-forming liquids, the term for this invention generically embraces semi-solids and viscus fluids. The pore-formers can be inorganic or organic. The term pore-former for both solids and liquids include substances that can be dissolved, extracted or leached from the precursor microporous wall by fluid present in the environment of use to form open-celled type microporous lamina. The pore-forming solids have a size, e.g., of about 0.1 to 200 microns and they include alkali metal salts such as lithium carbonate, sodium chloride, sodium bromide, potassium chloride, potassium sulfate, potassium phosphate, sodium acetate, sodium citrate, suitable calcium salts, and the like. Organic compounds such as polysaccharides including the sugars sucrose, glucose, fructose, mannitol, mannose, galactose, sorbitol and the like. They can be polymers soluble in the environment of use such as Carbowaxes®, Carbopol®, and the like. The pore-formers embrace diols, polyols, polyhydric alcohols, polyalkylene glycols, polyglycols, poly(a-w)alkylenediols, and the like. The pore-formers are non-toxic and on their removal from lamina, channels and pores are formed through the lamina that fill with fluid present in the environment use.

The controlled release coatings of the present invention may also include an exit means comprising at least one passageway, orifice, or the like. The passageway may be formed by such methods as those disclosed in U.S. Pat. Nos. 3,845,770; 3,916,889; 4,063,064; and 4,088,864 (all of which are hereby incorporated by reference). The passageway can have any shape such as round, triangular, square, elliptical, irregular, etc.

In addition to the inclusion of one or more drugs having a aqueous solubility of less than or equal to about 5 mg/ml, the controlled release formulations of the present invention can also include one or more drugs which are highly soluble in water relative to the insoluble drug. These relatively soluble drugs can be incorporated into the immediate release tablet core. The rate of release for such soluble drugs will depend upon the sustained release film coat, and is not dependent upon the core being rapidly dissolvable and/or disintegratable. Examples of such relatively soluble drugs which may be included in the controlled release formulations of the present invention include antihistamines (e.g., dimenhydrinate, diphenhydramine, chlorpheniramine and dexchlorpheniramine maleate), analgesics (e.g., aspirin, codeine, morphine, dihydromorphone, oxycodone, etc.), non-steroidal anti-inflammatory agents (e.g., naproxen, diclofenac, ibuprofen, aspirin, sulindac), gastrointestinals and anti-emetics (e.g., metoclopramide), anti-epileptics (e.g., phenytoin, meprobamate and nitrezepam), vasodilators (e.g., papaverine, diltiazem), cholinergics (e.g., neostigmine, pyridostigmine), anti-tussive agents and expectorants (e.g., codeine phosphate), antituberculosis agents (e.g., isoniazid), anti-spasmodics (e.g. atropine, scopolamine), anti-muscarinics (e.g., anisotropine), hormones (e.g., insulin, heparin), diuretics (e.g., bendrofluazide), anti-hypertensives (e.g., propranolol, clonidine), bronchodilators (e.g., albuterol), iron preparations (e.g., ferrous gluconate), anti-inflammatory steroids (e.g., hydrocortisone, triamcinolone, prednisone), antibiotics (e.g., penicillin v, tetracycline, clindamycin, novobiocin, metronidazde, cloxacillin), antihemorrhoidals, antidiarrheals, mucolytics, sedatives, decongestants, laxatives, antacids, vitamins (e.g., ascorbic acid), sympathomimetics (e.g., ephedrine, phenylpropanolamine). The above list is not meant to be exclusive.

In one preferred embodiment of the invention, the insoluble therapeutically active agent is acetaminophen, and the soluble therapeutically active agent is selected from the group consisting of hydromorphone, oxycodone, dihydrocodeine, codeine, dihydromorphine, morphine, buprenorphine, other opioids, salts of any of the foregoing, and mixtures of any of the foregoing.

In certain preferred embodiments of the present invention, the immediate release tablet core comprises from about 300 mg to about 500 mg acetaminophen and from about 5 to about 10 mg oxycodone, and preferably about 325 mg acetaminophen and about 10 mg oxycodone. In other preferred embodiments, the formulations of the present invention include form about 300 mg to about 500 mg (and preferably about 450 mg) acetaminophen together with from about 15 mg to about 60 mg (and preferably about 45 mg) codeine phosphate. In such embodiments, the tablet core will allow the dissolution of not less than 75% of the labeled amounts of acetaminophen and codeine phosphate hemihydrate when the tablet core placed in 900 ml 0.1 N hydrochloric acid for 45 minutes, as set forth in USP XXII. The amount of drug dissolved is determined using the assay method set forth in the Official Monograph for acetaminophen and codeine phosphate tablets set forth in USP XXII.

Immediate release APAP tablets or tablet cores may be prepared by wet granulating acetaminophen powder with a binder, then drying and sieving the resultant granules. Thereafter, a suitable adjuvant and lubricant are added and mixed. The mixture is then compressed.

DETAILED DESCRIPTION OF PREFERRED EMBODIMENTS

The following examples illustrate various aspects of the present invention. They are not to be construed to limit the claims in any manner whatsoever.

EXAMPLES 1–2

Immediate Release APAP Cores Overcoated with Controlled Release Coating

Immediate release APAP tablets are prepared by mixing the Acetaminophen powder with polyvinylpyrrolidone for 5 minutes in a Collette mixer. Then the powders are granulated using an appropriate amount of purified water.

After the batch is granulated, the wet granulation is dried in a fluid bed dryer at 60° C. inlet air temperature until the granulation is sufficiently dry for screening. When the granulation is sufficiently dry, it is passed through a Comil using a suitable screen size. The granulation is then placed in a V-Blender, the lactose is then added and mixed. The tablets are compressed to a weight of about 664.5 mg per tablet.

The coating suspension is prepared by dispersing Methocel E5 premium (commercially available from, e.g., Dow Chemical Co., St. Louis, Mo.) in 3 times its weight of boiling purified water while mixing for about 10–20 minutes. Thereafter, sufficient purified water at ambient temperature is added to the mixture such that the final concentration of the coating suspension is about 20% w/w. The coating suspension is mixed for about one to one and one-half hours until the methocel (hydroxypropylmethylcellulose) is completely dispersed. Then the methocel dispersion is cooled while mixing to a temperature below about 40° C.

In a separate container, a plasticizer (i.e., triethyl citrate) is mixed with Aquacoat ECD-30 suspension for about 15 minutes. Then, the Aquacoat ECD-30 dispersion is added to the Methocel dispersion and mixed for about 15 minutes to insure a thorough mixing. Afterwards, water is added, if necessary, to replace any water which had been lost by evaporation.

The immediate release tablets are then coated in an Accela Cota Pan using an appropriate spray gun and fittings. The spraying is continued until the tablets attain the required weight gain (in Example 1, to a weight gain of about 5%; in Example 2, to a weight gain of about 10%), by periodically weighing a small sample during the coating process. The coated tablets are cured in a curing oven at 60° C./80% RH for a minimum of about 3 days.

The final composition of the Tablets of Examples 1–2 are set forth in Tables 1 and 2 below, respectively.

TABLE 1

EXAMPLE 1 - APAP IMMEDIATE RELEASE TABLETS OVERCOATED TO A 5% WEIGHT GAIN

| Theoretical Amt/Tablet (mg) | | Ingredients |
|---|---|---|
| 500 | | Acetaminophen powder |
| 40 | | PVP |
| 123 | | Lactose, Hydrogen, spray dried |
| 1.5 | | Magnesium stearate |
| 16.6 | (of solids) | Aquacoat ECD-30 (as a 30% w/w suspension) |
| 16.6 | | Methocel E5 premium |
| 6.6 | | Triethyl citrate (PG) |
| q.s. | | Purified water |

TABLE 2

EXAMPLE 2 - APAP IMMEDIATE RELEASE TABLETS OVERCOATED TO A 10% WEIGHT GAIN

| Theoretical Amt/tab. (mg) | Ingredients |
|---|---|
| 500 | Acetaminophen powder |
| 40 | PVP |
| 123 | Lactose, Hydrogen, spray dried |
| 1.5 | Magnesium stearate |
| 33.2 | Aquacoat ECD-30 (As a 30% w/w suspension) |
| 33.2 | Methocel E5 premium |
| 13.3 | Triethyl citrate (PG) |
| q.s. | Purified water |

Next, tablets of Examples 1 and 2 are subjected to dissolution testing. The dissolution testing is carried out via the USP Basket Method, 37° C., 100 RPM, as previously described. The mean tablet weights of Examples 1 and 2 were 716 mg and 756.7 mg, respectively. The results are set forth in Tables 3–4 below, respectively.

TABLE 3

DISSOLUTION RESULTS OF EXAMPLE 1 APAP 500 MG TABLETS WITH CONTROLLED RELEASE AQUACOAT/METHOCOL 50:50 COATING TO A 5% WT GAIN CURED 3 DAYS AT 60° C./80% RH

| Hours | Percent Dissolved (Mean) |
|---|---|
| 1 | 5.4 |
| 2 | 11.8 |
| 4 | 22.2 |
| 8 | 41.8 |
| 12 | 60.0 |
| 18 | 82.0 |
| 24 | 98.3 |

TABLE 4

DISSOLUTION RESULTS OF EXAMPLE 2
APAP 500 MG TABLETS WITH CONTROLLED
RELEASE AQUACOAT/METHOCOL 50:50 COATING
TO A 10% WT GAIN CURED 3 DAYS AT 60° C./80% RH

| Hours | Percent Dissolved (Mean) |
|---|---|
| 1 | 2.7 |
| 2 | 6.6 |
| 4 | 14.0 |
| 8 | 27.2 |
| 12 | 40.2 |
| 18 | 57.8 |
| 24 | 73.6 |

EXAMPLES 3–4

Reproducibility of Dissolution Results—Immediate Release APAP Cores Overcoated with Controlled Release Coating Using Same Lot of Acetaminophen Powder In order to determine whether the dissolution profiles obtained from batch-to-batch would be acceptably similar when using the same lot of acetaminophen powder raw material or a different lot of the same grade of acetaminophen powder or further still a different grade of acetaminophen powder with a smaller particle size, the following examples were prepared:

In Examples 3 and 4, using the same lot of APAP powder, new batches of the tablets of Examples 1–2 (immediate release APAP tablets overcoated with controlled release coating) are made in order to determine whether the dissolution profiles obtained from batch-to-batch and using the same lot of acetaminophen powder would be acceptable. The tablets are manufactured, coated and cured in the same manner as set forth above with respect to Examples 1–2. The tablets of Example 3 are coated to a weight gain of about 5% (mean tablet weight 712.7 mg), whereas the tablets of Example 4 are coated to a weight gain of about 10% (mean tablet weight 757.6 mg). Thereafter, dissolution testing via the same USP Basket Method, 37° C., 100 RPM, as previously described, was conducted. The results are set forth in Tables 5–6 below, respectively.

TABLE 5

DISSOLUTION RESULTS OF EXAMPLE 3 - APAP 500 MG TABLETS
WITH CONTROLLED RELEASE AQUACOAT/METHOCOL 50:50
COATING TO A 5% WT GAIN CURED 3 DAYS USING SAME LOT
ACETAMINOPHEN POWDER AS IN EXAMPLE 1 AT 60° C./80% RH

| Hours | Percent Dissolved (Mean) |
|---|---|
| 1 | 8.5 |
| 2 | 14.0 |
| 4 | 23.5 |
| 8 | 41.3 |
| 12 | 58.2 |
| 18 | 80.6 |
| 24 | 99.8 |

TABLE 6

DISSOLUTION RESULTS OF EXAMPLE 4 - APAP 500 MG TABLETS
WITH CONTROLLED RELEASE AQUACOAT/METHOCOL 50:50
COATING TO A 10% WT GAIN CURED 3 DAYS USING SAME LOT
ACETAMINOPHEN POWDER AS IN EXAMPLE 2 AT 60° C./80% RH

| Hours | Percent Dissolved (Mean) |
|---|---|
| 1 | 3.9 |
| 2 | 7.8 |
| 4 | 16.0 |
| 8 | 30.2 |
| 12 | 43.8 |
| 18 | 62.6 |
| 24 | 77.1 |

The dissolution profiles of the tablets of Example 3 proved to be substantially similar to the dissolution profiles of the tablets of Example 1. Likewise, the dissolution profiles of the tablets of Example 4 proved to be substantially similar to the dissolution profiles of the tablets of Example 2. The results indicate that the batch-to-batch variation with respect to dissolution and using the same lot of acetaminophen powder would be acceptable when developing a controlled release product of a relatively insoluble drug for commercial use, e.g., to governmental regulatory authorities such as the United States Food and Drug Administration (F.D.A.).

EXAMPLES 5–6

Reproducibility of Dissolution Results—Immediate Release APAP Cores Overcoated with Controlled Release Coating Using a Different Lot of Acetaminophen Powder In Examples 5 and 6, new batches are made of the tablets of Examples 1–2 (immediate release APAP tablets overcoated with controlled release coating) in order to determine whether the dissolution profiles obtained from batch to batch and using a different lot of acetaminophen powder, would be acceptably similar. The tablets are manufactured, coated and cured in the same manner as set forth above with respect to Examples 1–2. The tablets of Example 5 are coated to a weight gain of about 5% (mean tablet weight 711.3 mg), whereas the tablets of Example 6 are coated to a weight gain of about 10% (mean tablet weight 745.8 mg). Thereafter, dissolution testing via the same USP Basket Method, 37° C., 100 RPM, as previously described, was conducted. The results are set forth in Tables 7–8 below, respectively.

TABLE 7

DISSOLUTION RESULTS OF EXAMPLE 5 - APAP 500 MG TABLETS
WITH CONTROLLED RELEASE AQUACOAT/METHOCEL
50:50 COATING TO A 5% WEIGHT GAIN CURED 3 DAYS AT
60° C./80% RH USING A DIFFERENT LOT OF ACETAMINOPHEN
POWDER

| Hours | Percent Dissolved (Mean) |
|---|---|
| 1 | 6.5 |
| 2 | 13.1 |
| 4 | 23.7 |
| 8 | 43.9 |
| 12 | 61.4 |
| 18 | 82.9 |
| 24 | 100.0 |

TABLE 8

DISSOLUTION RESULTS OF EXAMPLE 6 - APAP 500 MG TABLETS WITH CONTROLLED RELEASE AQUACOAT/METHOCEL 50:50 COATING TO A 10% WEIGHT GAIN CURED 3 DAYS AT 60° C./80% RH USING A DIFFERENT LOT OF ACETAMINOPHEN POWDER

| Hours | Percent Dissolved (Mean) |
|---|---|
| 1 | 3.3 |
| 2 | 7.5 |
| 4 | 15.5 |
| 8 | 29.3 |
| 12 | 42.5 |
| 18 | 60.9 |
| 24 | 77.1 |

The dissolution profiles of the tablets of Example 5 proved to be substantially similar to the dissolution profile of the tablets of Example 1. Likewise, the dissolution profiles of the tablets of Example 6 proved to be substantially similar to the dissolution profiles of the tablets of Example 2.

The results indicate that the batch-to-batch variation with respect to dissolution and using a different lot of acetaminophen powder would be acceptable when developing a controlled release product, thus indicating that such a product is reproducible and would meet FDA requirements.

EXAMPLES 7–8

Reproducibility of Dissolution Results—Immediate Release APAP Cores Overcoated with Controlled Release Coating Using Acetaminophen Powder of a Finer Particle Size In Examples 7 and 8, new batches are made of the tablets of Examples 1–2 (immediate release APAP tablets overcoated with controlled release coating) in order to determine whether the dissolution profiles obtained using a finer particle size acetaminophen powder, would be acceptably similar to the dissolution profiles of Examples 1 and 2. The tablets are manufactured, coated and cured in the same manner as set forth above with respect to Examples 1–2. The tablets of Example 7 are coated to a weight gain of about 5% (mean tablet weight 711.5 mg), whereas the tablets of Example 8 are coated to a weight gain of about 10% (mean tablet weight 751.7 mg). Thereafter, dissolution testing via the same USP Basket Method, 37° C., 100 RPM, as previously described was conducted. The results are set forth in Tables 9–10 below, respectively.

TABLE 9

DISSOLUTION RESULTS OF EXAMPLE 7 - APAP 500 MG TABLETS WITH CONTROLLED RELEASE AQUACOAT/METHOCEL 50:50 COATING TO A 5% WEIGHT GAIN CURED 3 DAYS AT 60° C./80% RH USING ACETAMINOPHEN POWDER OF A FINER PARTICLE SIZE

| Hours | Percent Dissolved (Mean) |
|---|---|
| 1 | 7.1 |
| 2 | 13.4 |
| 4 | 24.3 |
| 8 | 44.8 |
| 12 | 63.8 |
| 18 | 87.9 |
| 24 | 103.7 |

TABLE 10

DISSOLUTION RESULTS OF EXAMPLE 8 - APAP 500 MG TABLETS WITH CONTROLLED RELEASE AQUACOAT/METHOCEL 50:50 COATING TO A 10% WEIGHT GAIN CURED 3 DAYS AT 60° C./80% RH USING ACETAMINOPHEN POWDER OF A FINER PARTICLE SIZE

| Hours | Percent Dissolved (Mean) |
|---|---|
| 1 | 3.5 |
| 2 | 8.0 |
| 4 | 15.6 |
| 8 | 29.4 |
| 12 | 43.0 |
| 18 | 61.6 |
| 24 | 76.0 |

The dissolution profiles of the tablets of Example 7 proved to be substantially similar to the dissolution profiles of the tablets of Example 1. Likewise, the dissolution profiles of the tablets of Example 8 proved to be substantially similar to the dissolution profiles of the tablets of Example 2.

Figure 2:
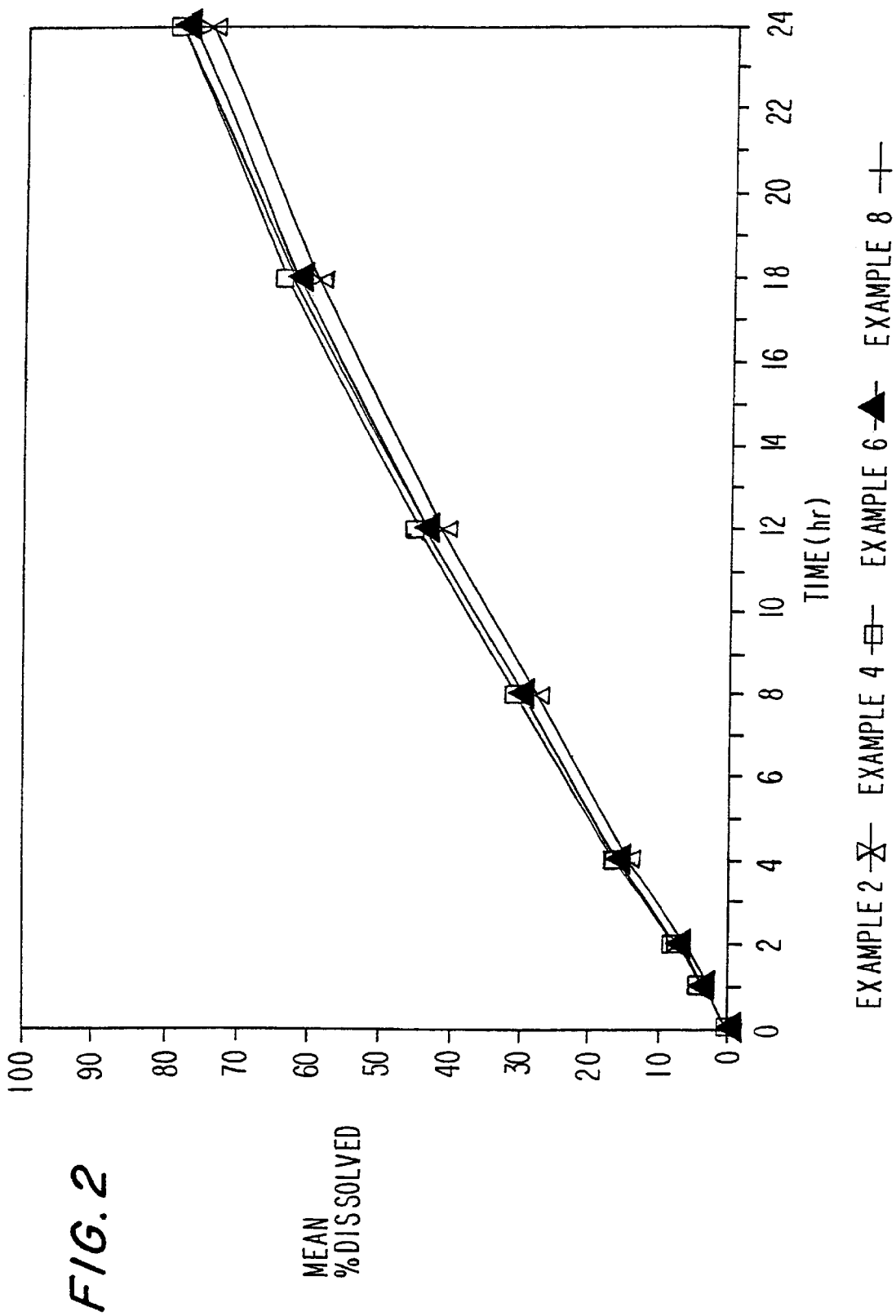
FIG. 2 is a graphical representation of the dissolution obtained for Examples 2, 4, 6 and 8.

The results indicate that variation with respect to dissolution using a different (finer) particle size acetaminophen powder would be acceptable when developing a controlled release product, which is a surprising finding for water-insoluble drugs. The data for all of the examples for the 5% controlled release coatings are also represented graphically in FIG. 1. From FIG. 1, it can be observed that the dissolution from Examples 1, 3, 5 and 7 are virtually superimposible. Thus showing excellent reproducibility from one batch to a second batch with the same raw material or a different lot of raw material, or even another lot of raw material of different particle size. Similarly, the results for the 10% controlled release coatings of the tablets from Examples 2, 4, 6 and 8 are shown in FIG. 2.

EXAMPLES 9–10

Reproducibility of Dissolution Results Immediate Release Codeine/APAP Cores Overcoated with Controlled Release Coating In order to determine whether the dissolution profiles obtained would be acceptably similar if a second active ingredient was incorporated in the immediate release core, Examples 9 and 10, were prepared, wherein new batches are made of the tablets of Examples 1–2 (immediate release APAP tablets overcoated with controlled release coating), but with the exception of incorporating codeine base in the powder mixture with acetaminophen and polyvinylpyrrolidone prior to the 5 minute dry mix. Codeine phosphate is a relatively soluble drug in comparison to APAP.

The tablets are manufactured, coated and cured in the same manner as set forth above with respect to Examples 1-2. The tablets of Example 9 are coated to a weight gain of about 5% (mean tablet weight 758.6 mg), whereas the tablets of Example 10 are coated to a weight gain of about 10% (mean tablet weight 799.4 mg). Thereafter dissolution testing via the same USP Basket Method, 37° C., 100 RPM, as previously described was conducted.

The final composition of the tablets of Examples 9–10 are set forth in Tables 11–12 below. The dissolution results for Example 9 are set forth in Tables 13–14 below, and the dissolution results for Example 10 are set forth in Tables 15 and 16 below (dissolution reported separately for APAP and codeine).

TABLE 11

EXAMPLE 9 - CODEINE/APAP IMMEDIATE RELEASE TABLETS OVERCOATED TO A 5% WEIGHT GAIN

| Theoretical Amt/Tablet (mg) | Ingredient |
|---|---|
| 35.94 | codeine base, monohydrate |
| 500 | Acetaminophen powder |
| 40 | PVP |
| 123 | Lactose, Hydrous, Spray dried |
| 1.5 | Magnesium stearate |
| 17.51 (of solids) | Aquacoat ECD-30 (as a 30% w/w suspension) |
| 17.51 | Methocel E5 premium |
| 7.00 | Triethyl citrate (PG) |
| q.s. | purified water |
| 742.46 (Total) | |

TABLE 12

EXAMPLE 10 - CODEINE/APAP IMMEDIATE RELEASE TABLETS OVERCOATED TO A 10% WEIGHT GAIN

| Theoretical Amt/Tablet (mg) | Ingredient |
|---|---|
| 35.94 | codeine base, monohydrate |
| 500 | Acetaminophen powder |
| 40 | PVP |
| 123 | Lactose, Hydrous, Spray dried |
| 1.5 | Magnesium stearate |
| 35.02 (of solids) | Aquacoat ECD-30 (as a 30% w/w suspension) |
| 35.02 | Methocel E5 premium |
| 14.01 | Triethyl citrate (PG) |
| q.s. | purified water |
| 784.49 (Total) | |

TABLE 13

DISSOLUTION RESULTS OF EXAMPLE 9 - APAP 500 MG TABLETS WITH CONTROLLED RELEASE AQUACOAT/METHOCEL 50:50 COATING TO A 5% WEIGHT GAIN CURED 3 DAYS AT 60° C./80% RH PERCENT ACETAMINOPHEN DISSOLVED

| Hours | Percent Dissolved (Mean) |
|---|---|
| 1 | 10.0 |
| 2 | 13.5 |
| 4 | 23.7 |
| 8 | 41.8 |
| 12 | 57.8 |
| 18 | 76.4 |
| 24 | 91.4 |

TABLE 14

DISSOLUTION RESULTS OF EXAMPLE 9 - APAP 500 MG TABLETS WITH CONTROLLED RELEASE AQUACOAT/METHOCEL 50:50 COATING TO A 5% WEIGHT GAIN CURED 3 DAYS AT 60° C./80% RH PERCENT CODEINE PHOSPHATE DISSOLVED

| Hours | Percent Dissolved (Mean) |
|---|---|
| 1 | 17.1 |
| 2 | 26.3 |
| 4 | 40.2 |
| 8 | 60.7 |
| 12 | 76.3 |
| 18 | 92.0 |
| 24 | 101.1 |

TABLE 15

DISSOLUTION RESULTS OF EXAMPLE 10 - APAP 500 MG TABLETS WITH CONTROLLED RELEASE AQUACOAT/METHOCEL 50:50 COATING TO A 10% WEIGHT GAIN CURED 3 DAYS AT 60° C./80% RH PERCENT ACETAMINOPHEN DISSOLVED

| Hours | Percent Dissolved (Mean) |
|---|---|
| 1 | 3.6 |
| 2 | 8.0 |
| 4 | 16.6 |
| 8 | 31.6 |
| 12 | 45.9 |
| 18 | 64.3 |
| 24 | 79.1 |

TABLE 16

DISSOLUTION RESULTS OF EXAMPLE 10 - APAP 500 MG TABLETS WITH CONTROLLED RELEASE AQUACOAT/METHOCEL 50:50 COATING TO A 10% WEIGHT GAIN CURED 3 DAYS AT 60° C./80% RH PERCENT CODEINE PHOSPHATE DISSOLVED

| Hours | Percent Dissolved (Mean) |
|---|---|
| 1 | 10.8 |
| 2 | 19.8 |
| 4 | 33.5 |
| 8 | 52.9 |
| 12 | 68.1 |
| 18 | 84.9 |
| 24 | 96.2 |

Figure 3:
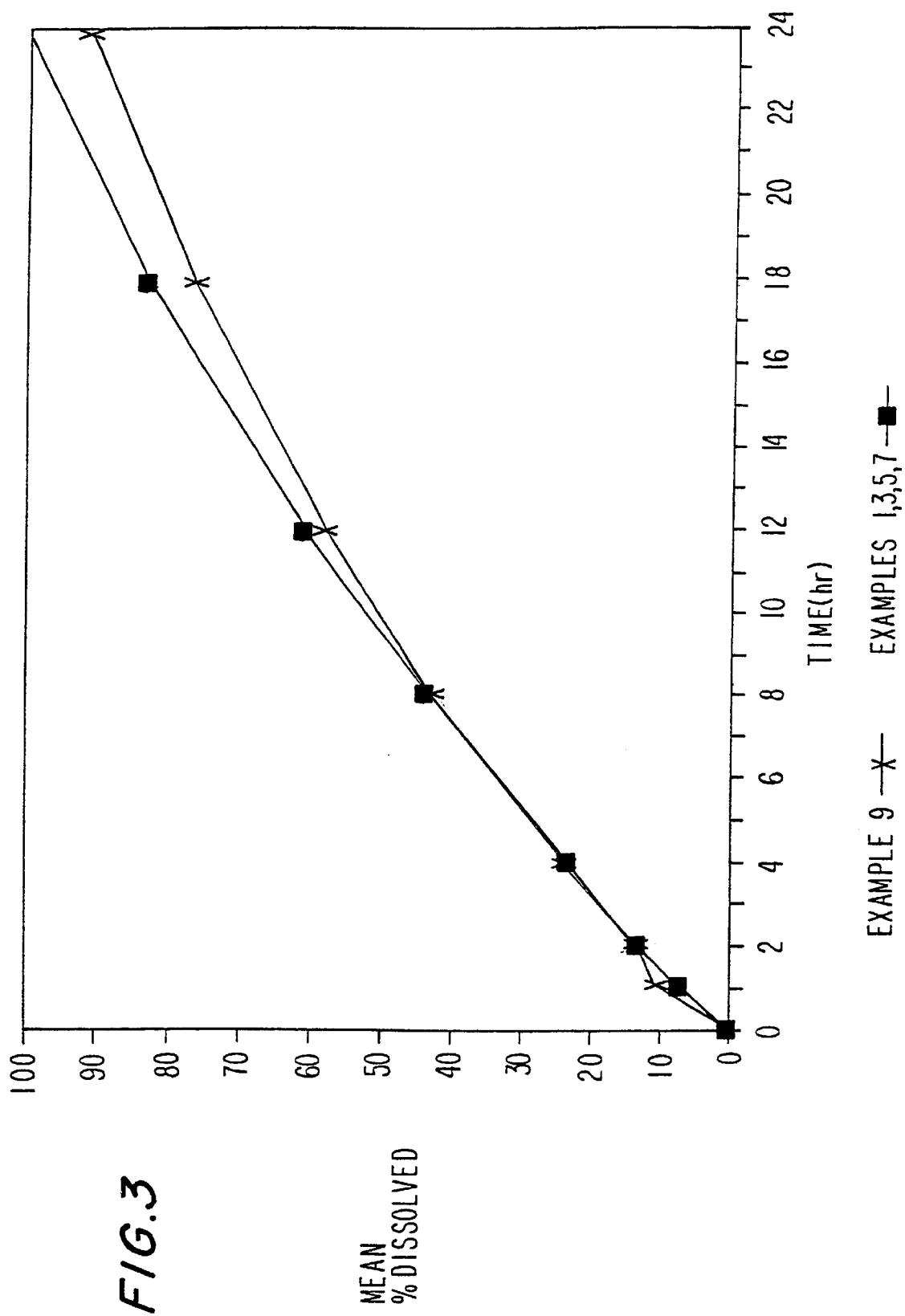
FIG. 3 is a graphical representation comparing the dissolution of Example 9 to the dissolution obtained for Examples 1, 3, 5 and 7.
Figure 4:
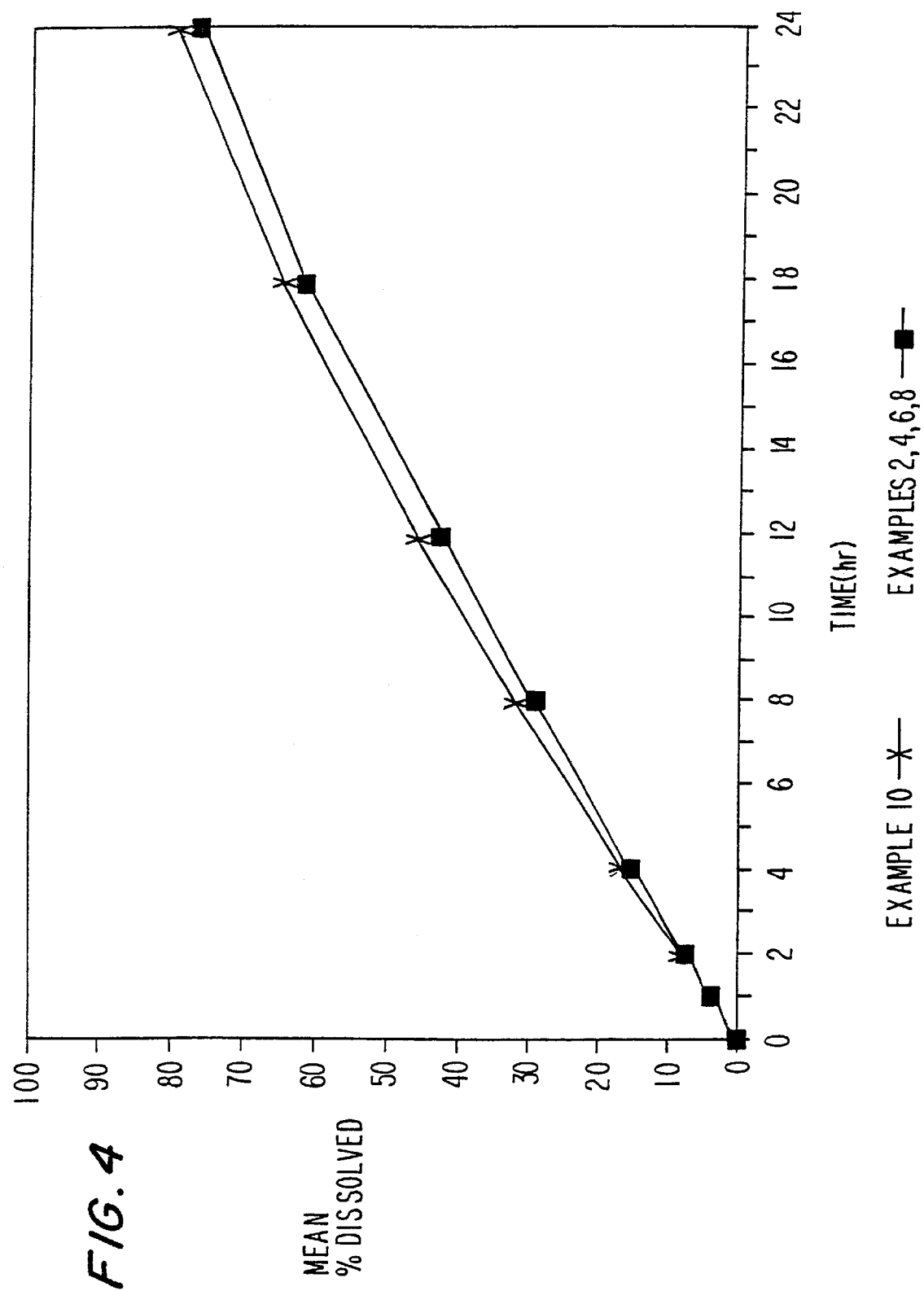
FIG. 4 is a graphical representation comparing the dissolution of Example 10 to the dissolution obtained for Examples 2, 4, 6 and 8.

The dissolution profiles of APAP in the tablets of Example 9 proved to be substantially similar to the dissolution profiles of the tablets of Examples 1, 3, 5 and 7. Likewise, this data is shown in FIG. 3. APAP in the tablets of Example 10 proved to be substantially similar to the dissolution profiles of the tablets of Examples 2, 4, 6 and 8. This data is shown in FIG. 4.

The results indicate that the controlled release coating is the controlling factor in the dissolution irrespective of the additional drug substance content of the core.

COMPARATIVE EXAMPLES 11–12

Controlled Release Matrix Tablets—Codeine Phosphate 45 Mg/APAP 450 Mg

In Comparative Examples 11–12, two separate batches of controlled release matrix tablets of codeine phosphate/APAP having identical formulas and manufacturing techniques are prepared in order to compare the dissolution profiles of the final product on a batch-to-batch basis.

The final product of Comparative Examples 11 and 12 have the composition set forth in Table 17 below.

TABLE 17

COMPOSITION OF COMPARATIVE EXAMPLES 11–12

| Amt/tab (mg) | Ingredients |
|---|---|
| 46 mg* | Codeine Phosphate, hemihydrate |
| 450 mg | Acetaminophen |
| 60 mg | Pregelatinized corn starch |
| 120 mg | Cetostearyl alcohol |
| 9 mg | Talc |
| 6 mg | Magnesium stearate |
| 21 mg | Opadry blue YS-1-4026 |
| q.s. | Purified water |
| 712 mg (Total) | |

*Equivalent to 45 mg of codeine phosphate, anhydrous.

The tablets of Comparative Examples 11–12 are prepared as follows. Codeine Phosphate, APAP and pregelatinized corn starch are mixed for about 5 minutes in a Collette Mixer. Then, the powders are granulated using an appropriate amount of purified water. After the batch is granulated, the wet granulation is dried in a fluid bed dryer at 60° C. inlet air temperature until granulation is sufficiently dry for screening. When the granulation is dry enough, it is passed through a #8 mesh screen, and then placed in the Collette Mixer.

The required amount of cetostearyl alcohol is melted and then the melted wax is incorporated into the granulation while mixing for about 1 minute. The waxed granulation is cooled to room temperature, and then passed through a #12 mesh screen. After screening, the granulation is placed in the Collette mixer and lubricated with talc and magnesium stearate. The granulation is then compressed into tablets of the appropriate weight and hardness.

The appropriate amount of film coating suspension is prepared by dispersing Opadry Blue YS-1-4026 in a sufficient amount of purified water, and then film coated in a rotary pan.

The above procedure is followed identically for a separate batch of tablets identified herein as Comparative Example 12.

Tablets of Comparative Example 11 (mean tablet weight 696.6 mg) are then subjected to dissolution testing. The dissolution testing is carried out separately with respect to the two drugs in the formulation, codeine phosphate and APAP, in order to determine the rate of in vitro release of each of these drugs from the formulation. The dissolution testing is carried out via the USP Basket Method, 37° C., 100 RPM, as previously described. The results are set forth in Tables 18 and 19 below.

TABLE 18

COMPARATIVE EXAMPLE 11 CODEINE PHOS./APAP 45/450 MG CONTROLLED RELEASE MATRIX TABLETS PERCENT ACETAMINOPHEN DISSOLVED

| Hours | Percent Dissolved (Mean) |
|---|---|
| 1 | 18.0 |
| 2 | 42.5 |

TABLE 18-continued

COMPARATIVE EXAMPLE 11 CODEINE PHOS./APAP 45/450 MG CONTROLLED RELEASE MATRIX TABLETS PERCENT ACETAMINOPHEN DISSOLVED

| Hours | Percent Dissolved (Mean) |
|---|---|
| 4 | 82.2 |
| 8 | 96.8 |
| 12 | 100.1 |
| 18 | 101.2 |
| 24 | 102.0 |

TABLE 19

COMPARATIVE EXAMPLE 11 CODEINE PHOS./APAP 45/450 MG CONTROLLED RELEASE MATRIX TABLETS PERCENT CODEINE PHOSPHATE DISSOLVED

| Hours | Percent Dissolved (Mean) |
|---|---|
| 1 | 37.5 |
| 2 | 69.0 |
| 4 | 99.3 |
| 8 | 101.4 |
| 12 | 101.9 |
| 18 | 102.3 |
| 24 | 103.5 |

Dissolution tests were identically carried out for the tablets of Comparative Example 12 (mean tablet weight 714 mg). The results are set forth in Tables 20 and 21 below.

TABLE 20

COMPARATIVE EXAMPLE 12 CODEINE PHOS./APAP 45 MG/450 MG CONTROLLED RELEASE MATRIX TABLETS PERCENT ACETAMINOPHEN DISSOLVED

| Hours | Percent Dissolved (Mean) |
|---|---|
| 1 | 14.9 |
| 2 | 29.7 |
| 4 | 63.9 |
| 8 | 89.4 |
| 2 | 94.3 |

TABLE 21

COMPARATIVE EXAMPLE 12 CODEINE PHOS./APAP 45 MG/450 MG CONTROLLED RELEASE MATRIX TABLETS PERCENT CODEINE PHOSPHATE DISSOLVED

| Hours | Percent Dissolved (Mean) |
|---|---|
| 1 | 34.0 |
| 2 | 59.4 |
| 4 | 94.8 |
| 8 | 98.4 |
| 12 | 99.4 |

Figure 5:
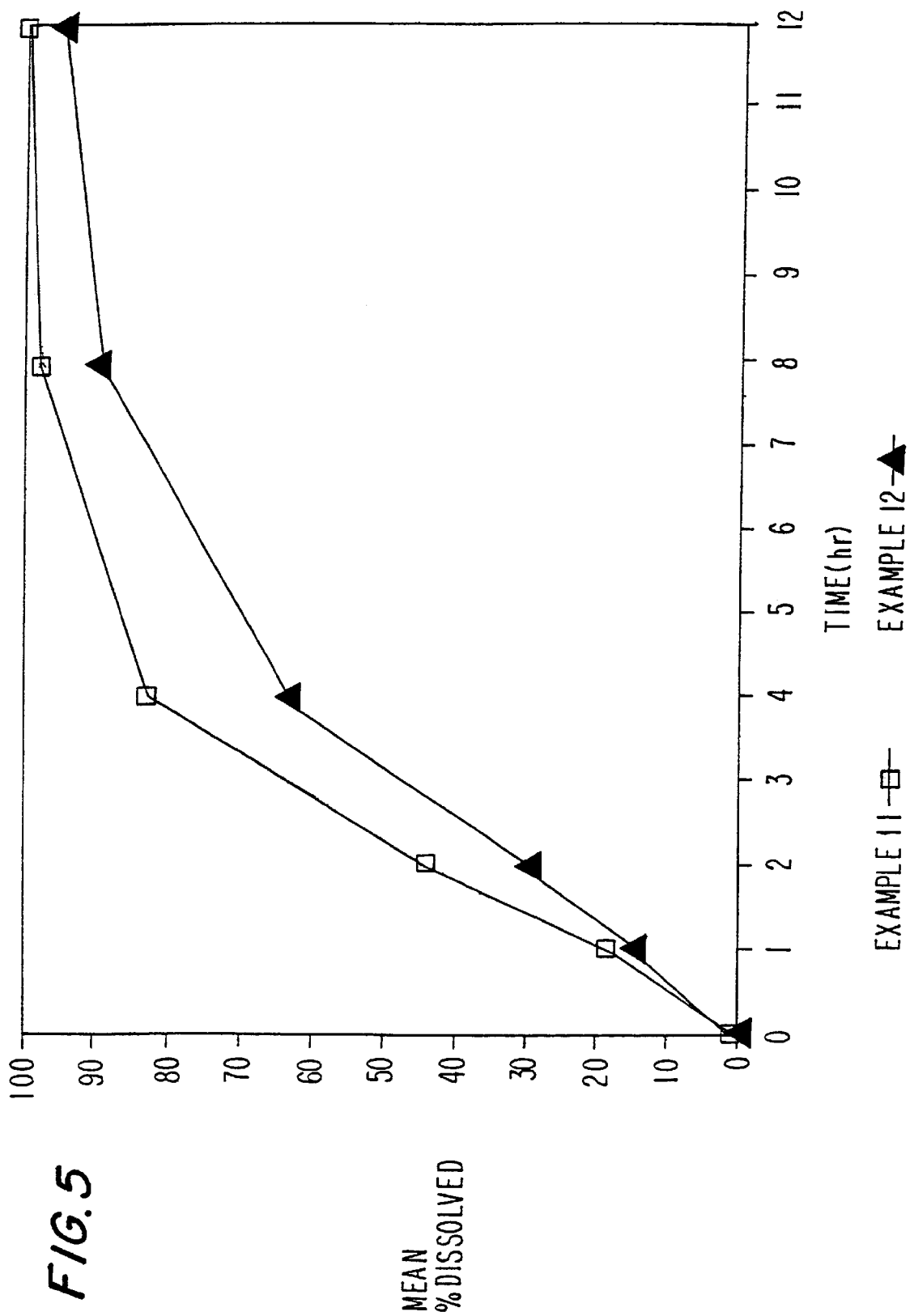
FIG. 5 is a graphical representation of the dissolution obtained for Comparative Example 11.
Figure 6:
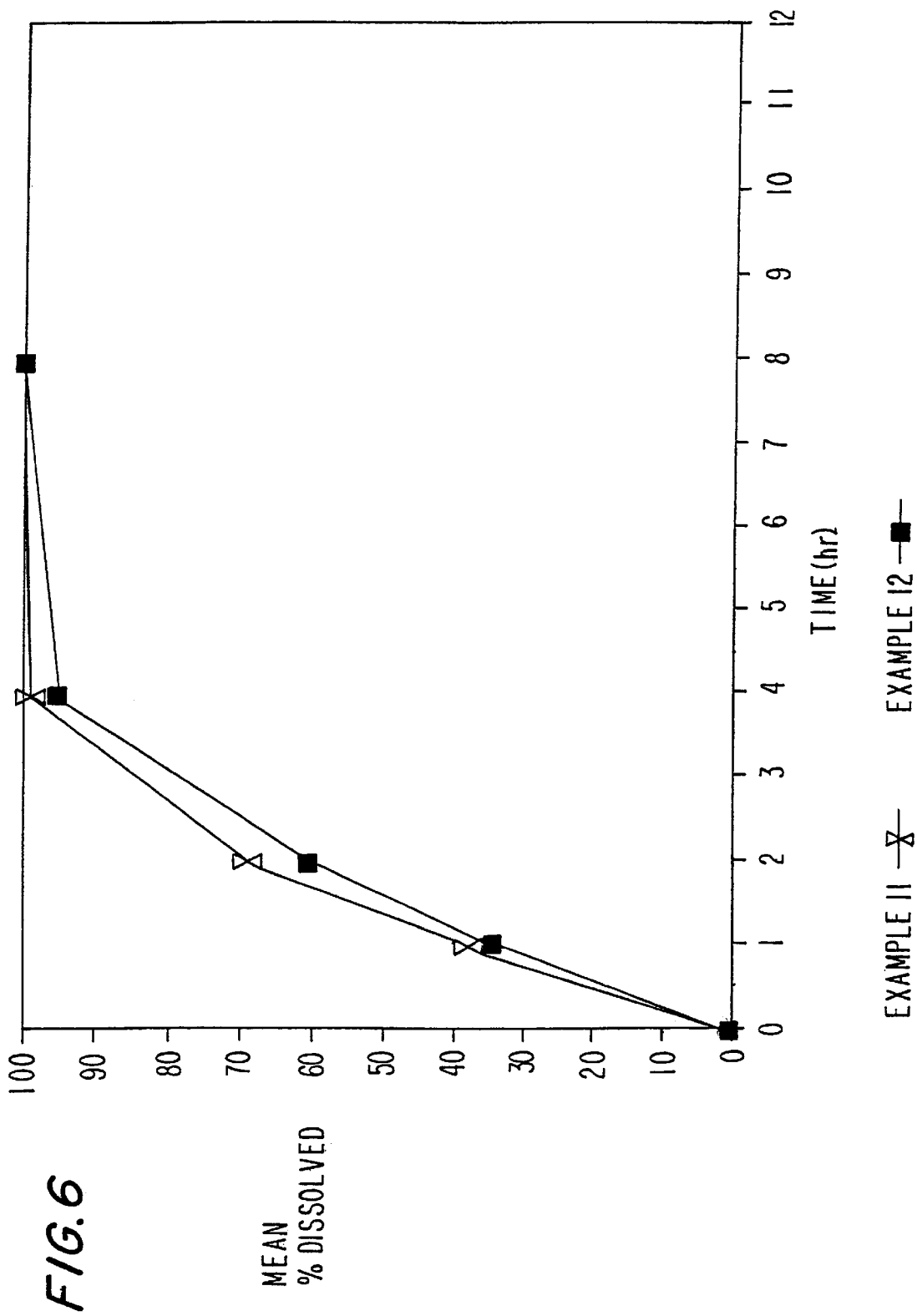
FIG. 6 is a graphical representation of the dissolution obtained for Comparative Example 12.

The dissolution profiles for codeine phosphate and APAP from the formulation of Comparative Examples 11 and 12 is graphically depicted in FIGS. 5 and 6. As can be readily ascertained, the batch-to-batch in vitro dissolution variability for the formulation with respect to the relatively soluble drug, codeine phosphate, was acceptably small. However, the batch-to-batch in vitro dissolution variability for the formulation with respect to the relatively insoluble drug, APAP, was unacceptably large.

COMPARATIVE EXAMPLES 13–14

Controlled Release Matrix Tablets Codeine Phosphate 45 Mg/APAP 450 Mg

In Comparative Examples 13–14, two separate batches of controlled release matrix tablets of codeine phosphate/APAP having identical formulas and manufacturing techniques are prepared in order to compare the dissolution profiles of the final product on a batch-to-batch basis. The formulations of Comparative Examples 13–14, while also relying upon a controlled release matrix to control the release of the drugs from the formulation, are formulated somewhat differently. The final product of Comparative Examples 13 and 14 have the composition set forth in Table 22 below.

TABLE 22

COMPOSITION OF COMPARATIVE EXAMPLES 13–14

| Amt/tab (mg) | Ingredients |
|---|---|
| 46 mg* | Codeine Phosphate, hemihydrate |
| 450 mg | Acetaminophen |
| 60 mg | Pregelatinized corn starch |
| 4 mg | Acdisol |
| 40 mg | Cetostearyl alcohol |
| 40 mg | Carbowax 8000 |
| 9 mg | Talc |
| 3 mg | Magnesium stearate |
| 20 mg | Opadry blue YS-1-4026 |
| q.s. | Purified water |
| 672 mg | (Total) |

*Equivalent to 45 mg of codeine phosphate, anhydrous.

Comparative Examples 13–14 are prepared as follows. Codeine Phosphate, APAP, Acdisol and pregelatinized corn starch are mixed for about 5 minutes in a Collette Mixer. The mixed powders are then granulated using an appropriate amount of purified water. After the batch is granulated, the wet granulation is dried in a fluid bed dryer until the granulation is sufficiently dry for screening. When the granulation is dry enough, it is passed through a screen and then placed in the Collette Mixer. The required amount of cetostearyl alcohol and Carbowax 8000 is melted, and then the melted wax is incorporated into the granulation while mixing. The waxed granulation is cooled to room temperature, and then passed through a 12 mesh screen. After screening, the granulation is placed in the Collette Mixer and lubricated with talc and magnesium stearate while mixing. The granulation is compressed at the appropriate weight.

The appropriate amount of film coating suspension is prepared by dispersing Opadry Blue YS-1-4026 in sufficient purified water and then the batch is film-coated in a rotary pan. After the tablets are coated, they are cured in an incubator at 45° C. for 48 hours.

Tablets of Comparative Example 13 (mean tablet weight 663.7 mg) are then subjected to dissolution testing. The dissolution testing is carried out separately with respect to the two drugs in the formulation, codeine phosphate and APAP, in order to determine the rate of in vitro release of each of these drugs from the formulation. The dissolution testing is carried out via the USP Basket Method, as previously described. The results are set forth in Tables 23 and 24 below.

TABLE 23

COMPARATIVE EXAMPLE 13
CODEINE PHOS./APAP 45 MG/450 MG
CONTROLLED RELEASE MATRIX TABLETS
PERCENT ACETAMINOPHEN DISSOLVED

| Hours | Percent Dissolved (Mean) |
|---|---|
| 1 | 24.6 |
| 2 | 54.9 |
| 4 | 92.3 |
| 8 | 100.6 |
| 12 | 101.5 |
| 18 | 101.9 |
| 24 | 102.4 |

TABLE 24

COMPARATIVE EXAMPLE 13
CODEINE PHOS./APAP 45 MG/450 MG
CONTROLLED RELEASE MATRIX TABLETS
PERCENT CODEINE PHOSPHATE DISSOLVED

| Hours | Percent Dissolved (Mean) |
|---|---|
| 1 | 40.1 |
| 2 | 67.4 |
| 4 | 96.6 |
| 8 | 99.7 |
| 12 | 100.1 |
| 18 | 100.5 |
| 24 | 101.2 |

Dissolution tests were identically carried out for the tablets of Comparative Example 14 (mean tablet weight 680.7 mg). The results are set forth in Tables 25 and 26 below.

TABLE 25

COMPARATIVE EXAMPLE 14
CODEINE PHOS./APAP 45 MG/450 MG
CONTROLLED RELEASE MATRIX TABLETS
PERCENT ACETAMINOPHEN DISSOLVED

| Hours | Percent Dissolved (Mean) |
|---|---|
| 1 | 21.2 |
| 2 | 38.2 |
| 4 | 74.5 |
| 8 | 97.8 |
| 12 | 101.0 |
| 18 | 100.9 |
| 24 | 101.4 |

TABLE 26

COMPARATIVE EXAMPLE 14
CODEINE PHOS./APAP 45 MG/450 MG
CONTROLLED RELEASE MATRIX TABLETS
PERCENT CODEINE PHOSPHATE DISSOLVED

| Hours | Percent Dissolved (Mean) |
|---|---|
| 1 | 37 |
| 2 | 55.4 |

TABLE 26-continued

COMPARATIVE EXAMPLE 14
CODEINE PHOS./APAP 45 MG/450 MG
CONTROLLED RELEASE MATRIX TABLETS
PERCENT CODEINE PHOSPHATE DISSOLVED

| Hours | Percent Dissolved (Mean) |
|---|---|
| 4 | 89.3 |
| 8 | 102.2 |
| 12 | 102.7 |
| 18 | 102.6 |
| 24 | 102.4 |

As can be readily ascertained from the results provided above, the batch-to-batch in vitro dissolution variability for the formulation with respect to the relatively soluble drug, codeine phosphate, was acceptably small. However, the batch-to-batch in vitro dissolution variability for the formulation with respect to the relatively insoluble drug, APAP, was unacceptably large. This is shown graphically in FIGS. 7 and 8. The in vitro dissolution results of Comparative Examples 13–14 provide further confirmation with regard to the batch-to-batch dissolution variability problems which arise when attempting to formulate controlled release products of relatively insoluble drugs.

The examples provided above are not meant to be exclusive. Many other variations of the present invention would be obvious to those skilled in the art, and are contemplated to be within the scope of the appended claims.

What is claimed is:

1. A sustained release tablet for oral administration, comprising an immediate release tablet core including an insoluble therapeutically active agent having an aqueous solubility of less than or equal to about 5 mg/ml, said tablet core containing a sufficient amount of said therapeutically active agent to render a therapeutic effect;

a second therapeutically active agent in a sufficient amount to render a therapeutic effect, said second therapeutically active agent being relatively soluble in water compared to said insoluble therapeutically active agent and being selected from the group consisting of antihistamines, analgesics, anti-inflammatory agents, gastro-intestinals, anti-emetics, anti-epileptics, vasodilators, anti-tussive agents, expectorants, anti-asthmatics, anti-spasmodics, hormones, diuretics, anti-hypertensives, bronchodilators, anti-inflammatory steroids, antivirals, antibiotics, antihemorrhoidals, hypnotics, psychotropics, antidiarrheals, mucolytics, sedatives, decongestants, laxatives, antacids, vitamins, and stimulants; and, a film coating formed over said core, said film coating comprising a sufficient amount of a hydrophobic material to provide a sustained release of said therapeutically active agent when said coated tablet is exposed to aqueous solutions.

2. The tablet of claim 1, wherein said film coating is sufficient to permit a sustained release of said insoluble therapeutically active agent sufficient to provide a duration of effect of from about 8 to about 24 hours.

3. The tablet of claim 2, wherein said insoluble therapeutically active agent is selected from the group consisting of naproxen and indomethacin.

4. A sustained release tablet for oral administration, comprising an immediate release tablet core including an insoluble therapeutically active agent having an aqueous solubility of less than or equal to about 5 mg/ml, said tablet core containing a sufficient amount of said therapeutically active agent to render a therapeutic effect; and, a film coating formed over said core, said film coating comprising a sufficient amount of a hydrophobic material to provide a sustained release of said therapeutically active agent when said coated tablet is exposed to aqueous solutions;

wherein said hydrophobic material is selected from the group consisting of a plasticized pharmaceutically acceptable acrylic polymer and a plasticized ethylcellulose.

5. The tablet of claim 1, wherein said second therapeutically active agent is selected from the group consisting of hydromorphone, oxycodone, dihydrocodeine, codeine, dihydromorphine, morphine, buprenorphine, salts of any of the foregoing, and mixtures of any of the foregoing.

6. The tablet of claim 1, wherein said film coating comprises a plasticized pharmaceutically acceptable acrylic polymer.

7. The tablet of claim 1, wherein said film coating comprises plasticized ethylcellulose.

8. The tablet of claim 1, wherein said hydrophobic material is selected from the group consisting of wax, shellac, zein, fatty alcohols, hydrogenated vegetable oils, water-insoluble cellulosic materials, acrylic polymers, and mixtures of any of the foregoing.

9. The tablet of claim 8, which releases said insoluble therapeutically active agent over a time period of about 24 hours when exposed to fluids in an environment of use.

10. The tablet of claim 5, wherein said second therapeutically active agent is codeine or oxycodone.

11. A sustained release tablet for oral administration, comprising an immediate release tablet core including an insoluble therapeutically active agent having an aqueous solubility of less than or equal to about 5 mg/ml, said tablet core containing a sufficient amount of said therapeutically active drug to render a therapeutic effect, said tablet core coated with a sustained release film coating comprising a hydrophobic material permitting a dissolution rate in vitro of the dosage form, when measured by the USP Paddle Method at 100 rpm in 900 ml aqueous buffer, pH between about 1.6 and about 7.2, at 37° C. between 12.5 and 42.5% (by wt) released after 1 hour, between 25 and 56% (by wt) released after 2 hours, between 45 and 75% (by wt) released after 4 hours and between 55 and 85% (by wt) released after 6 hours.

12. The tablet of claim 11, wherein said film coating is sufficient to permit a sustained release of said insoluble therapeutically active agent sufficient to provide a duration of effect of from about 12 to about 24 hours.

13. The tablet of claim 11, wherein said insoluble therapeutically active agent is selected from the group consisting of naproxen and indomethacin.

14. The tablet of claim 11, wherein said tablet core further comprises a second therapeutically active agent in a sufficient amount to render a therapeutic effect, said second therapeutically active agent being soluble in water relative to said insoluble therapeutically active agent and being selected from the group consisting of antihistamines, analgesics, anti-inflammatory agents, gastro-intestinals, anti-emetics, anti-epileptics, vasodilators, anti-tussive agents, expectorants, anti-asthmatics, antispasmodics, hormones, diuretics, anti-hypertensives, bronchodilators, anti-inflammatory steroids, antivirals, antibiotics, antihemorrhoidals, hypnotics, psychotropics, antidiarrheals, mucolytics, sedatives, decongestants, laxatives, antacids, vitamins, and stimulants.

15. The tablet of claim 14, wherein said second therapeutically active agent is selected from the group consisting of hydromorphone, oxycodone, dihydrocodeine, codeine, dihydromorphine, morphine, buprenorphine, salts of any of the foregoing, and mixtures of any of the foregoing.

16. The tablet of claim 15, comprising from about 5 to about 10 mg oxycodone.

17. The tablet of claim 12, wherein said film coating comprises an aqueous dispersion of a plasticized acrylic polymer cured at a temperature greater than the glass transition temperature of the aqueous dispersion of said plasticized acrylic polymer until an endpoint is reached at which said cured coated tablet provides a stable dissolution, said endpoint being determined by comparing the dissolution profile of said coated tablet immediately after curing to the dissolution profile of said coated tablet after exposure to accelerated storage conditions of three months at a temperature from about 37° C. to about 40° C. and a relative humidity from about 75% to about 80%.

18. The tablet of claim 12, wherein said film coating comprises an aqueous dispersion of plasticized ethylcellulose cured at a temperature greater than the glass transition temperature of the aqueous dispersion of said plasticized ethylcellulose and at from about 60% to about 100% relative humidity until an endpoint is reached at which said cured coated tablet provides a stable dissolution profile, said endpoint being determined by comparing the dissolution profile of said coated tablet immediately after curing to the dissolution profile of said coated tablet after exposure to accelerated storage conditions of three months at a temperature from about 37° C. to about 40° C. and a relative humidity from about 75% to about 80%.

19. The tablet of claim 11, wherein said tablet core is coated with said hydrophobic material to a weight gain level from about 3 to about 20 percent.

20. The tablet of claim 15, wherein said second therapeutically active agent is selected from the group consisting of from about 5 mg to about 10 mg oxycodone, and from about 15 mg to about 60 mg codeine phosphate.

21. A sustained release tablet for oral administration, comprising
an immediate release tablet core containing a sufficient amount of acetaminophen to render a therapeutic effect;
a second therapeutically active agent in a sufficient amount to render a therapeutic effect, said second therapeutically active agent being relatively soluble in water compared to said insoluble therapeutically active agent and being selected from the group consisting of antihistamines, analgesics, anti-inflammatory agents, gastro-intestinals, anti-emetics, anti-epileptics, vasodilators, anti-tussive agents, expectorants, anti-asthmatics, anti-spasmodics, hormones, diuretics, anti-hypertensives, bronchodilators, anti-inflammatory steroids, antivirals, antibiotics, antihemorrhoidals, hypnotics, psychotropics, antidiarrheals, mucolytics, sedatives, decongestants, laxatives, antacids, vitamins, and stimulants; and,
a film coating formed over said core, said film coating comprising a sufficient amount of a hydrophobic material to provide a sustained release of said therapeutically active agent when said coated tablet is exposed to aqueous solutions.

22. A sustained release tablet for oral administration, comprising
an immediate release tablet core containing a sufficient amount of acetaminophen to render a therapeutic effect, said tablet core coated with a sustained release film coating comprising a hydrophobic material permitting a dissolution rate in vitro of the dosage form, when measured by the USP Paddle Method at 200 rpm in 900 ml aqueous buffer, pH between about 1.6 and about 7.2, at 37° C. between 12.5 and 42.5% (by wt) released after 1 hour, between 25 and 56% (by wt) released after 2 hours, between 45 and 75% (by wt) released after 4 hours between 55 and 85% (by wt) released after 6 hours.

23. A sustained release tablet for oral administration, comprising
an immediate release tablet core containing a sufficient amount of acetaminophen to render a therapeutic effect; and,
a film coating formed over said core, said film coating comprising a sufficient amount of a hydrophobic material to provide a sustained release of said therapeutically active agent when said coated tablet is exposed to aqueous solutions;
wherein said hydrophobic material is selected from the group consisting of a plasticized pharmaceutically acceptable acrylic polymer and a plasticized ethylcellulose.

24. The tablet of claim 4, further comprising a second therapeutically active agent is selected from the group consisting of hydromorphone, oxycodone, dihydrocodeine, codeine, dihydromorphine, morphine, buprenorphine, salts of any of the foregoing, and mixtures of any of the foregoing.

25. The tablet of claim 21, wherein said second therapeutically active agent is selected from the group consisting of hydromorphone, oxycodone, dihydrocodeine, codeine, dihydromorphine, morphine, buprenorphine, salts of any of the foregoing, and mixtures of any of the foregoing.

26. The tablet of claim 22, further comprising a second therapeutically active agent is selected from the group consisting of hydromorphone, oxycodone, dihydrocodeine, codeine, dihydromorphine, morphine, buprenorphine, salts of any of the foregoing, and mixtures of any of the foregoing.

27. The tablet of claim 23, further comprising a second therapeutically active agent is selected from the group consisting of hydromorphone, oxycodone, dihydrocodeine, codeine, dihydromorphine, morphine, buprenorphine, salts of any of the foregoing, and mixtures of any of the foregoing.

* * * * *